United States Patent
Yeh et al.

(10) Patent No.: US 11,401,232 B2
(45) Date of Patent: Aug. 2, 2022

(54) MODIFIED CHROMIUM-DOPED ZINC GALLATE NANOCUBE, ITS PREPARATION METHOD AND USES THEREOF

(71) Applicant: National Cheng Kung University, Tainan (TW)

(72) Inventors: Chen-Sheng Yeh, Tainan (TW); Liu-Chun Wang, Tainan (TW); Zheng-Zhe Chen, Kaohsiung (TW); Ping-Ching Wu, Tainan (TW); Chia-Hao Su, Kaohsiung (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 299 days.

(21) Appl. No.: 16/907,159

(22) Filed: Jun. 19, 2020

(65) Prior Publication Data

US 2021/0395182 A1    Dec. 23, 2021

(51) Int. Cl.

| | | |
|---|---|---|
| *C07C 65/03* | (2006.01) | |
| *C07F 3/00* | (2006.01) | |
| *C07F 7/00* | (2006.01) | |
| *A61K 49/00* | (2006.01) | |
| *C07F 7/18* | (2006.01) | |
| *C07F 3/06* | (2006.01) | |
| *C09K 11/06* | (2006.01) | |
| *A61K 49/04* | (2006.01) | |
| *B82Y 15/00* | (2011.01) | |
| *B82Y 30/00* | (2011.01) | |
| *B82Y 40/00* | (2011.01) | |

(52) U.S. Cl.
CPC .......... *C07C 65/03* (2013.01); *A61K 49/0428* (2013.01); *C07F 3/06* (2013.01); *C07F 7/1804* (2013.01); *C09K 11/06* (2013.01); *B82Y 15/00* (2013.01); *B82Y 30/00* (2013.01); *B82Y 40/00* (2013.01); *C09K 2211/188* (2013.01)

(58) Field of Classification Search
CPC .......... C07C 65/03; C07F 3/06; C07F 7/1804; A61K 49/0428; C09K 11/06
See application file for complete search history.

(56) References Cited

PUBLICATIONS

Low Dose of X-Ray-Excited Long-Lasting Luminescent Concave Nanocubes in Highly Passive Targeting Deep-Seated Hepatic Tumors, Advanced Materials on Oct. 18, 2019.

*Primary Examiner* — Sikarl A Witherspoon
(74) *Attorney, Agent, or Firm* — NZ Carr Law Office PLLC

(57) ABSTRACT

Disclosed herein are modified chromium-dpoed zinc gallate (ZGC) nanocubes, which are characterized in respectively having a concave surface that is modified with (3-aminopropyl)triethoxysilane (APTES). The modified ZGC nanocubes produce long lasting luminescence (LLL) that lasts for at least 1.5 hours under X-ray or UV excitation. Also disclosed herein are methods for the preparation of the modified ZGC nanocubes; and methods for imaging an area of interest (e.g., cancer) in a live subject using the modified ZGC nanocubes as an imaging agent.

22 Claims, 19 Drawing Sheets
(9 of 19 Drawing Sheet(s) Filed in Color)

(G)

(H)

(I)

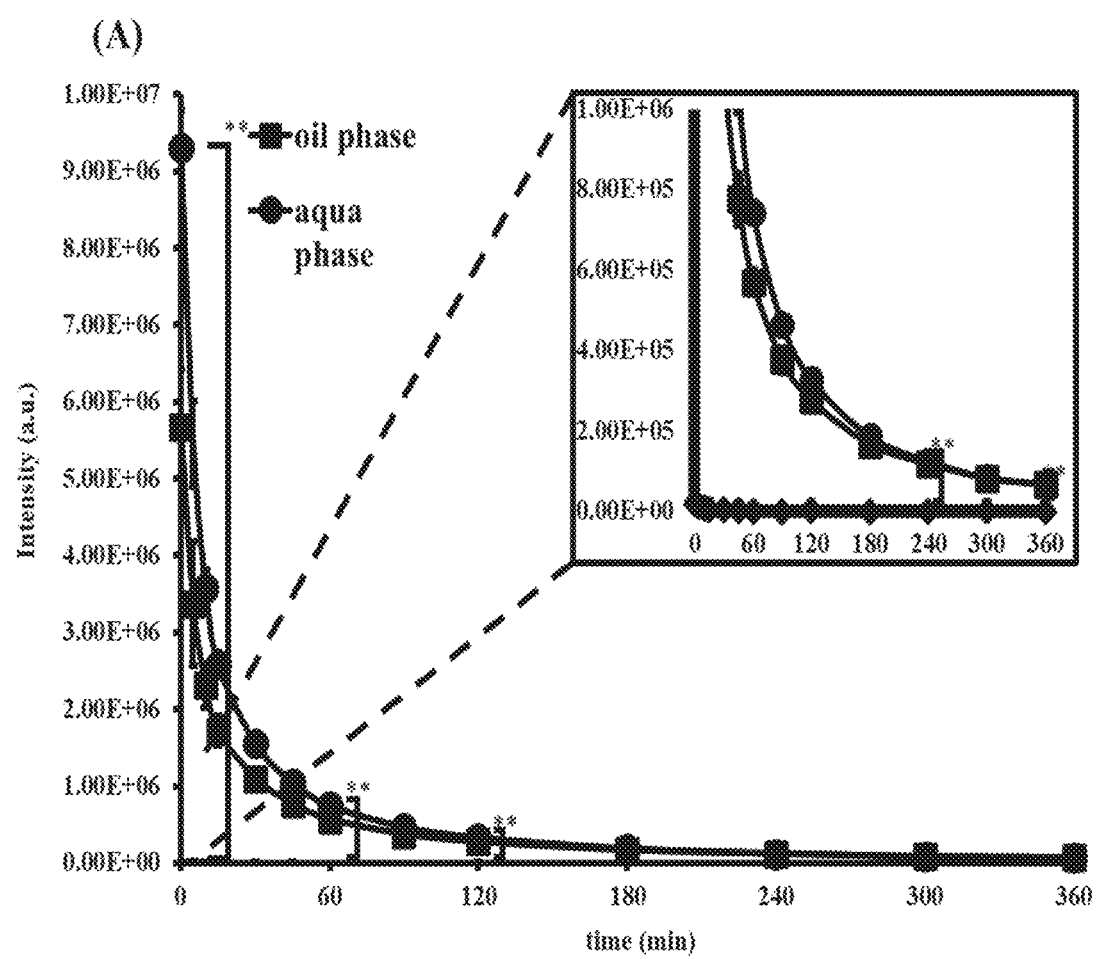

(B)

(C)

(D)

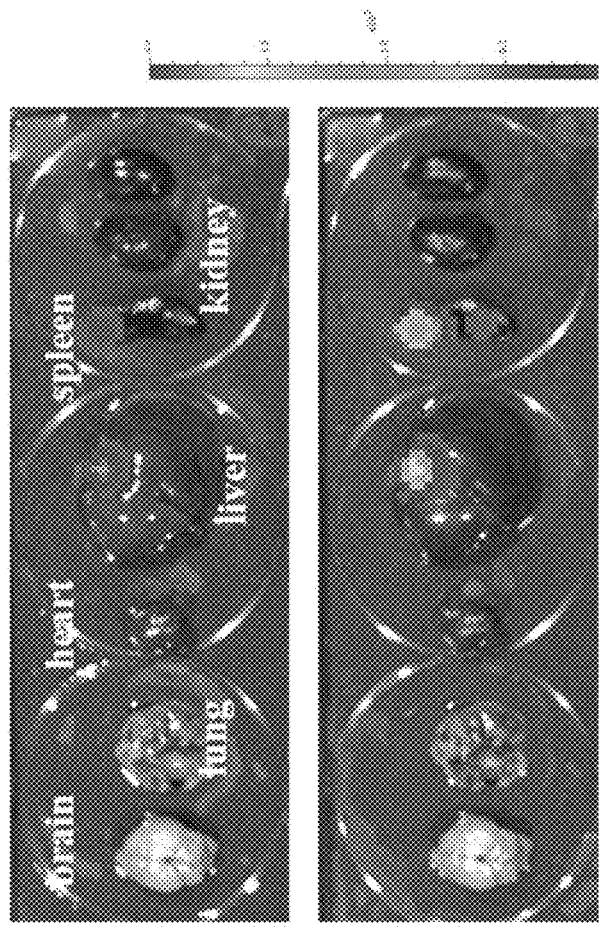
FIG 7 (B) afterglow after 4 h / re-excitation (0.5 Gy)

MODIFIED CHROMIUM-DOPED ZINC GALLATE NANOCUBE, ITS PREPARATION METHOD AND USES THEREOF

STATEMENT REGARDING PRIOR DISCLOSURES BY THE INVENTOR OR A JOINT INVENTOR UNDER 37 C.F.R. 1.77(B)(6)

Part of the subject matter of the invention described in the present application was published by the inventors, Chen-Sheng Yeh, Liu-Chun Wang, Zheng-Zhe Chen, and Chia-Hao Su in an article titled "Low Dose of X-Ray-Excited Long-Lasting Luminescent Concave Nanocubes in Highly Passive Targeting Deep-Seated Hepatic Tumors;" this article was published online by Advanced Materials on 18 Oct. 2019. Therefore, the publications or disclosures was made by and/or originated from all member of the inventive entity of the present invention less than one year before the filing date of the present application. A copy of the article is provided in a concurrently filed Information Disclosure Statement pursuant to the guidance of 78 Fed. Reg. 11076 (Feb. 14, 2013).

BACKGROUND OF THE INVENTION

1. Field of the Invention

The present disclosure relates to nanoprobes suitable for biological imaging. More particularly, the disclosure invention relates to modified chromium-doped zinc nanocubes, their production methods and uses thereof.

2. Description of Related Art

In vivo imaging faces two substantial challenges: the poor signal-to-noise (S/N) ratios due to tissue autofluorescence, and limited tissue penetration depth under in situ external excitation. To avoid tissue autofluorescence interference, several types of nanoprobes (e.g. $Ag_2S$, carbon nanotubes) have been developed to emit near-infrared (NIR) wavelengths in the tissue transparency window for in vivo imaging to eliminate background noise. Alternatively, the long-lasting luminescence (LLL) nanophosphors characterized by luminescence persisting after excitation has ceased can improve the S/N signal by removing tissue background noise from in situ excitation. Usually, the lifetime of the biological luminescent signal would decay completely in nanoseconds, thus the LLL could be collected after the short-lived biological background. LLL nanophosphors are materials capable of storing radiation in the form of trapped electrons and holes, slowly emitting photons following carrier recombination.

Another concern in biological imaging using nanoprobes is the choice of the external excitation source to overcome the penetration limitation. Accordingly, significant work has focused on the fabrication of nanometric light-absorbing materials such as upconversion nanocrystals and semiconducting quantum dots which can be activated by the NIR-I, -II, and -III wavelengths. Recent studies using chromium-doped zinc gallate have demonstrated that the LLL of $ZnGa_2O_4:Ce^{3+}$ (ZGC) can be illuminated by red light. However, red light or even NIR source still suffers from tissue penetration limitations. For example, the first NIR (NIR-I) biological window has only 1 mm penetration and the 1,064 nm residing in the second NIR (NIR-II) tissue transparency region displays penetration of 5 mm. Accordingly, X-ray sources would be the optimal choice for imaging deeper tissue.

To eliminate tissue autofluorescence interference and overcome the tissue penetration limitation for in situ excitation, nanophosphors exhibiting LLL subjected to X-ray excitation show considerable promise for in vivo imaging. However, few bioimaging studies have used X-rays as an excitation source in LLL nanophosphors. Most previous work has on long-lasting luminescence mechanisms. More recently, activation of ZGC in red light has shifted from ex vivo excitation to in vivo excitation for LLL nanophosphors in bioimaging. ZGC exhibits a cubic spinel structure and is viewed as one of the most representative LLL phosphors, excitable by UV and visible sources. The radioluminescence of X-ray irradiation (immediately or delayed), has also been seen in ZGC powder- and nanosized-forms. Unfortunately, nanoscale ZGC typically exhibits an agglomerative or clustered morphology lacking well-defined cubic shape.

Accordingly, there exist in this art a need of improved ZGC nanoprobes with long lasting luminescence suitable for imaging deeper tissue.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

According to one aspect of the present disclosure, there is provided a modified chromium-dpoed zinc gallate (ZGC) nanocube, which is characterized in having a concave surface modified with (3-aminopropyl)triethoxysilane (APTES).

Additionally or optionally, each of the modified ZGC nanocube further comprises a plurality of polyethylene glycol (PEG) molecules independently linked to the APTES via an amide bond formed there between.

According to embodiments of the present disclosure, the modified ZGC nanocubes or the pegylated, modified nanocubes independently produce long lasting luminescence (LLL) that lasts for at least 1.5 hours after being excited with a dose of X-ray, preferably, the LLL lasts for at least 3 hours; more preferably, the LLL lasts for at least 5 hours.

According to the second aspect of the present disclosure, there is provided a method of producing a modified ZGC nanocube. The method includes steps of:
  (a) respectively reacting zinc nitrate and gallium nitrate with a base, thereby forming zinc hydroxide and gallium hydroxide;
  (b) mixing the zinc hydroxide and the gallium hydroxide respectively produced in the step (a) and chromium nitrate with water to give a first mixture;
  (c) adding a chelating agent and toluene to the first mixture to give a second mixture;
  (d) autoclaving the second mixture to produce a ZGC nanocube; and
  (e) silanizing the ZGC nanocube with (3-aminopropyl)triethoxysilane (APTES) to produce the modified ZGC nanocube.

Examples of the base suitable for use in the step (a) include but are not limited to, ammonium hydroxide, sodium hydroxide, potassium hydroxide and the like.

The chelating agent suitable for use in the step (c) may be $C_{16-20}$ fatty acid, carboxylated PEG or ascorbic acid. Suitable examples of $C_{16-20}$ fatty acid include, but are not limited to, palmitic acid, oleic acid, margaric acid, stearic acid, nonadecanoic acid, eicosanoic acid, palmitoeic acid, elaidic acid, vaccenic acid, linoleic acid, linolelacidic acid, α-linolenic acid, stearidonic acid, paullinic acid, gondoic acid, mead acid, dihomo-γ-linolenic acid, and arachidonic acid.

According to embodiments of the present disclosure, in the step (d), the autoclave is conducted at a temperature of 220° C. for 3 days; and in the step (e), the silanization is conducted at a temperature of 60° C. for 18 hours.

According to optional embodiments of the present disclosure, the method may further include a step of pegylating the modified ZGC nanocube by reacting with amine-PEG-acid in the presence of 1-Ethyl-3-(3-dimethylaminopropyl) carbodiimide (EDC) and N-hydroxysuccinimide (NHS), thereby producing a pegylated modified ZGC nanocube, in which the amine-PEG-acid has a molecular weight of about 3,400.

According to preferred embodiments of the present disclosure, the modified ZGC nanocube and the pegylated modified ZGC nanocube respectively produce long lasting luminescence (LLL) that lasts for at least 1.5 hours after being excited with X-ray; preferably, the LLL lasts for at least 3 hours after being excited with X-ray; more preferably, the LLL lasts for at least 5 hours after being excited with X-ray.

According to the second aspect of the present disclosure, there is provided a method of imaging an area of interest (AOI) in a subject. The method includes steps of:
(a) administering a sufficient amount of the pegylated modified ZGC nanocube of the present disclosure to the AOI; and
(b) irradiating the subject with a dose of X ray thereby producing the image of the AOI.

According to embodiments of the present disclosure, in the step (b), the dose of X ray is no more than 3 Gy. Preferably, the dose of X ray is about 0.5 Gy.

According to embodiments of the present disclosure, the AOI is a cancer.

Examples of cancer suitable for imaging by the present method include, but are not limited to, bone cancer, brain cancer, breast cancer, colon cancer, cervical cancer, Ewing's sarcoma, esophageal cancer, hepatic cancer, head and neck cancer, larynx cancer, melanoma, multiple myeloma, nasopharynx cancer, non-small-cell lung cancer, non-melanoma skin cancer, neuroblastoma, pancreatic cancer, prostate cancer, retinoblastoma, rectal cancer, small-cell lung cancer, testicular cancer, thyroid cancer, and Wilms' tumor.

According to one preferred embodiment of the present disclosure, the cancer is hepatic cancer.

According to embodiments of the present disclosure, the subject is a mammal. Preferably, the subject is a human.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where.

DESCRIPTION

Figure 1:
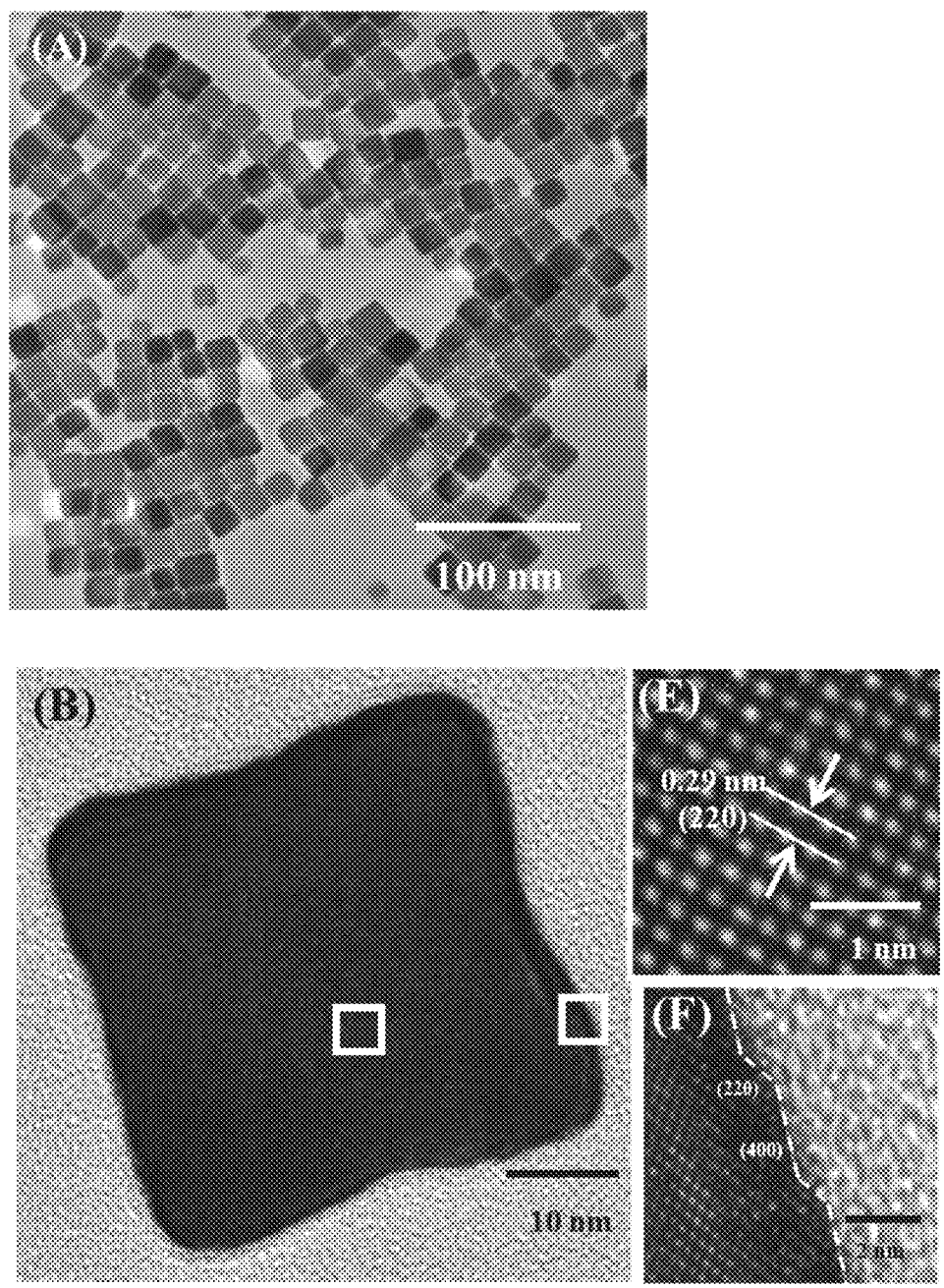
FIG. 1 Structural characterization and luminescence of ZGC nanocubes. (A) TEM image of ZGC nanocubes. (B) TEM image obtained from a single ZGC nanocube. (C) TEM images captured by titling from 5° to 30°. (D) Electron diffraction pattern of a single ZGC nanocube. (E) Lattice fringes showing {220} facet from the center of a single ZGC nanocube. (F) HRTEM image of an edge-on facet showing a combination of {220} and {400} facets. (G) XRD pattern of ZGC nanocubes. (H) Luminescent spectra of ZGC nanocubes excited by 250 nm as a function of Cr dopant concentration. (I) Different features taken by TEM for nanocubes before and after APTES modification in toluene and $H_2O$, respectively.
Figure 1:
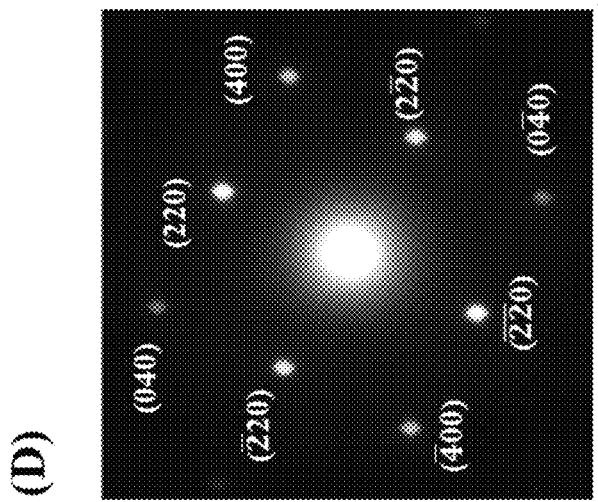
Figure 1:
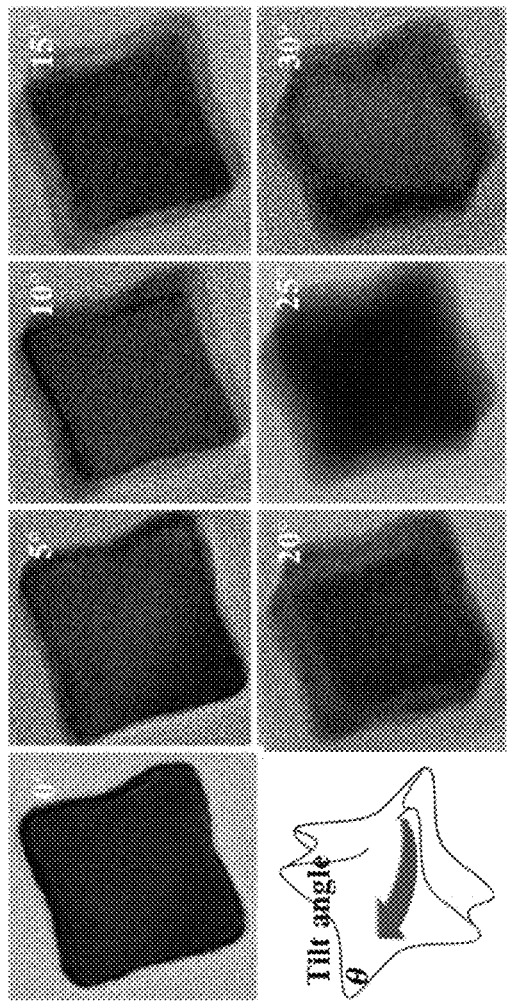
Figure 1:
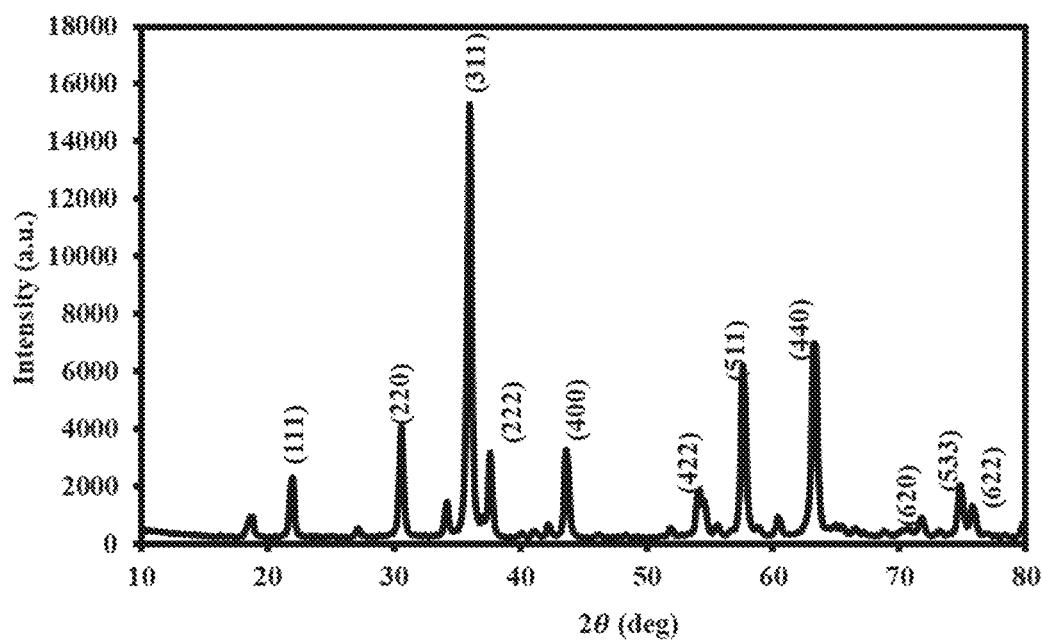
Figure 1:
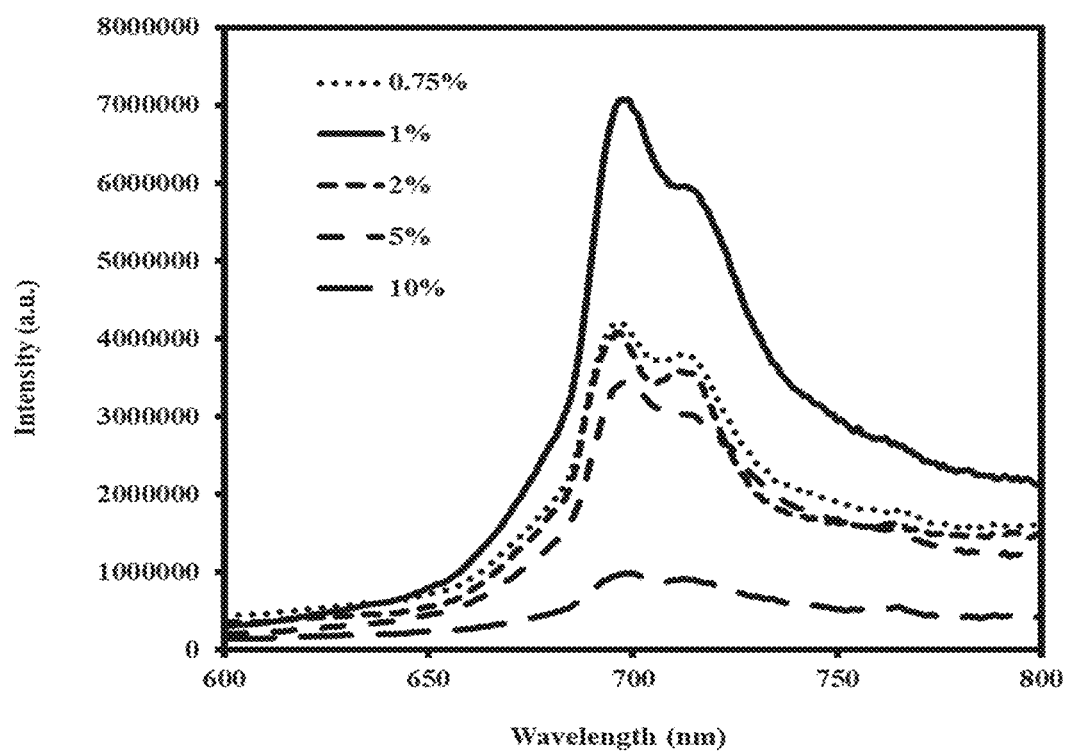
Figure 1:
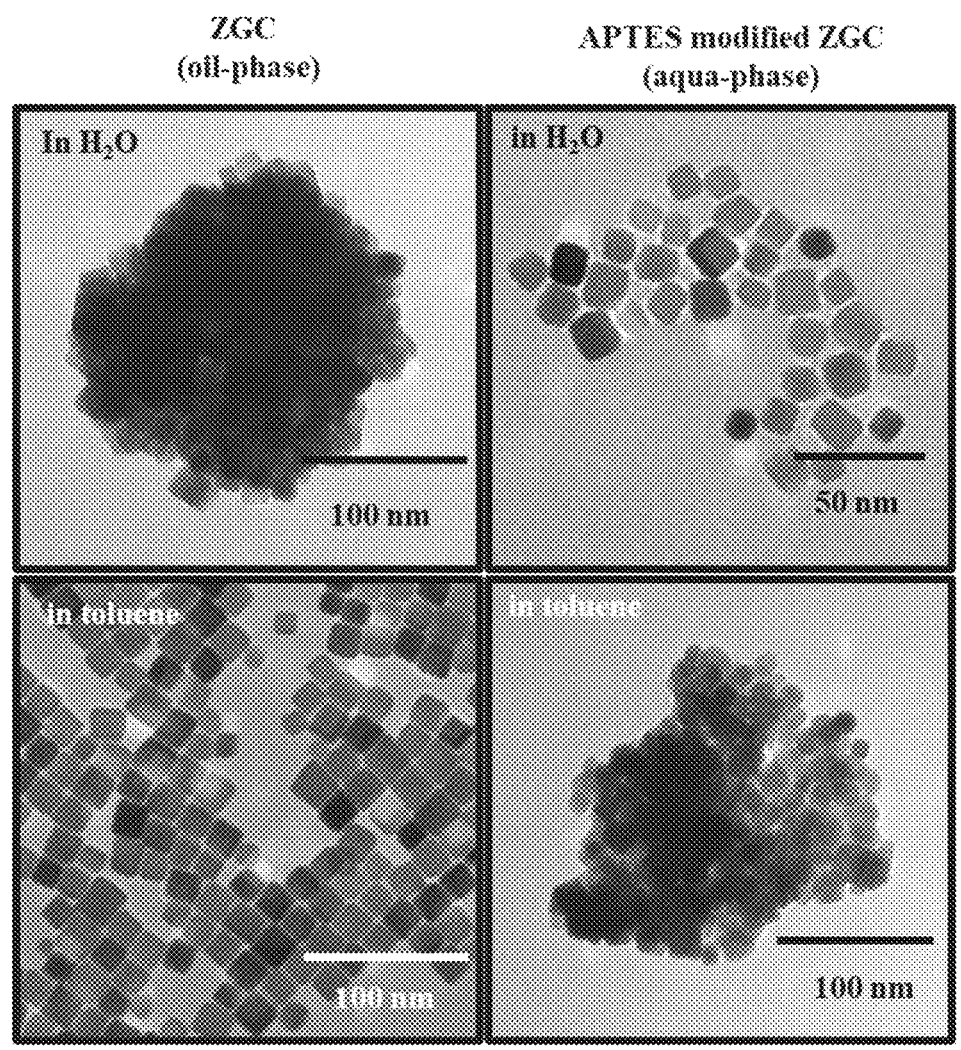

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the context of the present disclosure are collected here. Unless defined otherwise, all technical and scientific terms used herein have the same meaning as commonly understood by one of the ordinary skill in the art to which this invention belongs.

The term "subject" or "patient" is used interchangeably herein and is intended to mean a mammal including the human species that is treatable by the method of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the present invention. Examples of a "subject" or "patient" include, but are not limited to, a human, rat, mouse, guinea pig, monkey, pig, goat, cow, horse, dog, cat, bird and fowl. In a preferred embodiment, the subject is a human.

The term "administered", "administering" or "administration" are used interchangeably herein to refer a mode of delivery, including, without limitation, orally, intravenously, intramuscularly, intraperitoneally, intraarterially, subcutaneously, or transdermally administering an agent (e.g., a fibronectin inhibitor) of the present invention.

The term "a sufficient amount" as used herein refers to an amount sufficient, at dosages, and for periods of time necessary, to achieve the desired result with respect to imaging an area of interest (AOI) in a subject. Sufficient amount may be expressed, for example, in grams, milligrams, micrograms or nanograms; or as milligrams per kilogram of body weight (mg/Kg) or nanograms per kilogram of body weight (ng/Kg). Alternatively, the sufficient amount can be expressed in the concentration of the active component (e.g., the modified ZGC nanocubes of the present disclosure), such as molar concentration, mass concentration, volume concentration, molality, mole fraction, mass fraction and mixing ratio.

The term "carboxylated PEG" as used herein refers to carboxylic acid functionalized PEG molecule, in which after functionalization, the PEG molecule will comprise at least one carboxylic group in its structure.

The singular forms "a", "and", and "the" are used herein to include plural referents unless the context clearly dictates otherwise.

For convenience, certain terms employed in the specification, examples and appended claims are collected here. Unless defined otherwise, all technical and scientific terms used herein have the same meaning as commonly understood by one of the ordinary skilled in the art to which this invention belongs.

2. The Modified ZGC Nanocubes

Aspects of the present disclosure relate to the unexpected findings that modified ZGC nanocubes prepared by the method of the present disclosure exhibit a much stronger long-lasting luminescence (LLL) under UV or X-ray excitation. Further, uptake of the present modified ZGC nanocubes by cancerous cells is more significant than that of normal healthy cells. Accordingly, the present modified ZGC nanocubes may serve as an agent for imaging or identifying cancerous tissue in a subject.

The first aspect of the present disclosure thus is directed to a modified chromium-dpoed zinc gallate (ZGC) nanocube, which is characterized in having a concave surface modified with (3-aminopropyl)triethoxysilane (APTES).

According to embodiments of the present disclosure, the modification by ATES on the surface of the ZGC nanocube renders the ZGC nanocube hydrophilic, thereby allowing the modified ZGC nanocube capable of being dispersed in the water phase.

Additionally or optionally, the modified ZGC nanocube may further comprise a plurality of polyethylene glycol (PEG) molecules independently linked to the APTES via an amide bond formed there between.

According to embodiments of the present disclosure, the modified ZGC nanocube may produce long lasting luminescence (LLL) under UV or X-ray excitation.

In some embodiments, the modified ZGC nanocube is excited by a UV light, and produces LLL that lasts for at least 0.5 hr, such as 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, and 6.0 hours; preferably lasts for at least 3 hours, such as 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, and 6.0 hours; more preferably lasts for at least 5 hours, such 5.0, 5.1, 5.2, 5.3, 5.4, 5.5, 5.6, 5.7, 5.8, 5.9, and 6.0 hours. In other embodiments, the modified ZGC nanocube is excited by a dose of X-ray that is no more than 3 Gy, such as 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, and 2.9 Gy; preferably no more than 1.5 Gy, such as 0.1, 0.2, 0.3, 0.4, 0.5, 0.6, 0.7, 0.8, 0.9, 1.0, 1.1, 1.2, 1.3, and 1.4 Gy; more preferably no more than 0.8 Gy, such as 0.1, 0.2, 0.3, 0.4, 0.5, 0.6, and 0.7 Gy; and produces LLL that lasts for at least 0.5 hour, such as 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, and 6.0 hours; preferably lasts for at least 3 hours, such as 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, and 6.0 hours; more preferably lasts for at least 5 hours, such as 5.0, 5.1, 5.2, 5.3, 5.4, 5.5, 5.6, 5.7, 5.8, 5.9, and 6.0 hours. According to some embodiments of the present disclosure, no significant change to erythrocytes and platelets are found when exposed to X-ray irradiation dose of 5 Gy.

3. Preparation of the Modified ZGC Nanocubes

Also encompassed in the present disclosure is a method for the preparation of the afore-described modified ZGC nanocube. The method includes steps of:
  (a) respectively reacting zinc nitrate and gallium nitrate with a base, thereby forming zinc hydroxide and gallium hydroxide;
  (b) mixing the zinc hydroxide and the gallium hydroxide respectively produced in the step (a) and chromium nitrate with water to give a first mixture;
  (c) adding a chelating agent and toluene to the first mixture to give a second mixture;
  (d) autoclaving the second mixture to produce a ZGC nanocube; and
  (e) silanizing the ZGC nanocube with (3-aminopropyl) triethoxysilane (APTES) to produce the modified ZGC nanocube.

Examples of the base suitable for use in the step (a) include but are not limited to, ammonium hydroxide, sodium hydroxide, potassium hydroxide and the like.

The chelating agent suitable for use in the step (c) preferably comprises functional groups (e.g., —COOH or —OH) capable of binding with a metal ion. Examples of chelating agent suitable for use in the step (c) may be $C_{16-20}$ fatty acid, carboxylated PEG or ascorbic acid. Suitable examples of $C_{16-20}$ fatty acid include, but are not limited to, palmitic acid, oleic acid, margaric acid, stearic acid, nonadecanoic acid, eicosanoic acid, palmitoeic acid, elaidic acid, vaccenic acid, linoleic acid, linolelaidic acid, γ-linolenic acid, stearidonic acid, paullinic acid, gondoic acid, mead acid, dihomo-γ-linolenic acid, and arachidonic acid. Preferably, the chelating agent used in the step (c) is oleic acid.

According to embodiments of the present disclosure, in the step (d), the autoclave is conducted at a temperature of 220° C. for at least 72 hours, thereby gives ZGC nanocubes that are independently about 30 nm in diameter and a well-defined concave-cubic morphology. In the case when the autoclave is continued for only 12 hours, sphere-like shape ZGC particles are formed; in the case when the autoclave is continued for 48 hours, then nonocubic shape without well-defined edges are formed. Both the sphere-like shape ZGC particles and ZGC nanocubes without well-defined edges tend to agglomerate due to surface defects, and have negative impact on the optical properties (i.e., reduced LLL intensity or period).

To render the ZGC nanocubes produced in the step (d) suitable for bio application, the surface of each ZGC nanocubes are silanized by reacting with APTES at a temperature of 60° C. for 18 hours (i.e., the step (e)). The ZGC nanocubes having their surface modified with APTES are capable of being dispersed in water.

Additionally or optionally, the method may further include a step of pegylating the modified ZGC nanocubes (i.e., the step (f)). To this purpose, the ZGC nanocubes produced in the step (e) are reacted with amine-PEG-acid in the presence of 1-Ethyl-3-(3-dimethylaminopropyl)carbodiimide (EDC) and N-hydroxysuccinimide (NHS), thereby produces a pegylated modified ZGC nanocube. Preferably, the amine-PEG-acid used in the step (f) has a molecular weight of about 3,400.

According to preferred embodiments of the present disclosure, the modified ZGC nanocube produced in the step (e) or the pegylated modified ZGC nanocube produced in the step (f) independently produces long lasting luminescence (LLL) that lasts for at least 0.5 hour under X-ray or UV excitation. In some embodiments, the modified ZGC nanocube produced in the step (e) or the pegylated modified ZGC nanocube produced in the step (f) is excited by a UV light, and produces LLL that lasts for at least 0.5 hr, such as 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, and 6.0 hours; preferably lasts for at least 3 hours, such as 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, and 6.0 hours; more preferably lasts for at least 5 hours, such 5.0, 5.1, 5.2, 5.3, 5.4, 5.5, 5.6, 5.7, 5.8, 5.9, and 6.0 hours. In other embodiments, the modified ZGC nanocube produced in the step (e) or the pegylated modified ZGC nanocube produced in the step (f) is excited by a dose of X-ray that is no more than 3 Gy, such as 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, and 2.9 Gy; preferably no more than 1.5 Gy, such as 0.1, 0.2, 0.3, 0.4, 0.5, 0.6, 0.7, 0.8, 0.9, 1.0, 1.1, 1.2, 1.3, and 1.4 Gy; more preferably no more than 0.8 Gy, such as 0.1, 0.2, 0.3, 0.4, 0.5, 0.6, and 0.7 Gy; and produces LLL that lasts for at least 0.5 hour, such as 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, and 6.0 hours; preferably lasts for at least 3 hours, such as 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, and 6.0 hours; more preferably lasts for at least 5 hours, such as 5.0, 5.1, 5.2, 5.3, 5.4, 5.5, 5.6, 5.7, 5.8, 5.9, and 6.0 hours.

4. Use of the Present Modified ZGC Nanocubes

Also encompasses in the present disclosure is a method of imaging an area of interest (AOI) in a subject via use of the present modified ZGC nanocubes. The method includes steps of:
  (a) administering a sufficient amount of the pegylated modified ZGC nanocube of the present disclosure to the AOI; and
  (b) irradiating the subject with a dose of X ray thereby producing the image of the AOI.

According to embodiments of the present disclosure, the AOI is irradiated with a dose of X ray that is no more than 3 Gy. Preferably, the dose of X ray is about 0.5 Gy.

Preferably, the AOI is a cancer. Examples of cancer suitable for imaging by the present method include, but are not limited to, bone cancer, brain cancer, breast cancer, colon cancer, cervical cancer, Ewing's sarcoma, esophageal cancer, hepatic cancer, head and neck cancer, larynx cancer, melanoma, multiple myeloma, nasopharynx cancer, non-small-cell lung cancer, non-melanoma skin cancer, neuroblastoma, pancreatic cancer, prostate cancer, retinoblastoma, rectal cancer, small-cell lung cancer, testicular cancer, thyroid cancer, and Wilms' tumor.

According to one preferred embodiment of the present disclosure, the AOI is a hepatic cancer.

According to embodiments of the present disclosure, the subject is a mammal. Preferably, the subject is a human.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods

Preparation of ZnGa$_2$O$_4$:Cr (ZGC) Concave Nanocubes.

ZGC concave nanocubes were synthesized through a solvothermal process. Zn(OH)$_2$ and Ga(OH)$_3$ were prepared first as precursors, in which 1 mL and 1.5 mL of ammonium hydroxide were respectively added to Zn(NO$_3$)$_2$ and Ga(NO$_3$)$_3$ solution with subsequent stirring for 5 min, until gel-like precipitates were formed, which were washed with deionized water three times. Next, Zn(OH)$_2$ (9.9 mg), Ga(OH)$_3$ (24 mg) and Cr(NO$_3$)$_3$ (0.4 mg) were added to 10 mL of deionized water and stirred for 10 min at room temperature. Oleic acid (1 mL) and toluene (4.5 mL) were added into the mixture with subsequent stirring for 1 h. The mixture was then sealed in a Teflon-lined stainless autoclave, and maintained in a pre-heated oven at 220° C. for three days. The ZGC nanocubes were collected by centrifugation and washed with toluene three times. ZGC was dispersed in toluene.

Preparation of Agglomerative ZGC Nanoparticles.

The agglomerative nanoparticles dispersed in H$_2$O were synthesized in accordance with a procedure described previously (Wang et al., J. Am. Chem. Soc. 2015, 137, 5304). Briefly, ammonium hydroxide was added to a mixture containing Ga(NO$_3$)$_3$, Zn(NO$_3$)$_2$ and Cr(NO$_3$)$_3$, then vigorously stirred for 1 h. The solution was then transferred to an autoclave and kept in an oven at 220° C. for 10 h. The agglomerative ZGC nanoparticles were collected and washed with deionized water.

Preparation of APTES Modified ZGC Concave Nanocubes.

Silanization of ZGC with APTES was obtained following a surface modification. First, ZGC (1 mL, 300 ppm) in toluene was mixed with ethanol (7 mL), followed by an injection of (3-aminopropyl)triethoxysilane (APTES) (200 μL). The reaction was kept at 60° C. for 18 h. The APTES modified ZGC was collected by centrifugation and washed with ethanol three times.

PEGylated ZGC Concave Nanocubes.

The heterobifunctional amine-PEG-acid (NH$_2$-PEG-COOH, MW: 3400) was used for the PEGylation of ZGC nanocubes. To synthesize PEGylated ZGC nanocubes, the APTES modified ZGC nanocubes with NH$_2$ group (300 ppm) were mixed with COOH-PEG-NH$_2$ (1.36 mg) in ethanol (5 mL). The mixture was stirred for 10 min. Subsequently the EDC (1 mg) was added to the solvent and stirred for 30 min. Then NHS 1 mg) dissolved in de-ionized water was added to form stable amide bonds between APTES-modified ZGC and COOH-PEG-NH$_2$. The reaction was stirred for 4 h at room temperature. The obtained PEGylated ZGC was washed several times with ethanol and centrifuged to remove excess of PEG that is not being grafted onto the ZGC. The resulting PEGylated ZGC nanocubes possessed —NH$_2$ outward.

Mercury Lamp Excited Persistent Luminescent Property.

The ZGC (200 ppm) was put into a black 96-well plate, and the ZGC nanocubes were irradiated with a mercury lamp with a power density of 0.5 w cm$^{-2}$ for 1 min, and then allowed to sit for 60 s prior to IVIS imaging to monitor persistent luminescence. The IVIS exposure time was fixed at 30 s with a filter to collect emissions at 700 nm.

Synchrotron Radiation X-Ray Excited Radioluminescence.

Synchrotron radiation X-ray excited radioluminescence (SRXRL) was performed with a 15 KeV monochromatic beam at TPS 09A beamLine of Taiwan Photon Source (TPS). TPS is a 3 GeV synchrotron ring running with a current of 400 mA. The X-ray source of the TPS 09A beamLine is an in-vacuum undulator (IU22). A monochromatic X-ray is generated by double crystals, Si (111), monochromator with beam size 500×500 μm$^2$ (H×V) at sample position. The flux is 10$^{13}$ which is about 50.4 Gy sec$^{-1}$. SRXRL was also performed with a BL01C2 beamLine from Taiwan Light Source (TLS) using 15 KeV monochromatic X-ray. X-ray excited radioluminescence (XRL) measurements were run on 0.5 mm thick powdered samples on Scotch tape. For two experiments, light is collected via an optical fiber and measured with an HORIBA iHR550 imaging spectrometer equipped with a Syncerity CCD Camera. The spectrometer is calibrated according to the emission lines of Hg, 546, 577 and 579 nm, with a fluorescent lamp. The measurement used grating 1200 mm$^{-1}$.

In Vitro X-Ray Induced Persistent Luminescence Property.

The ZGC (200 ppm) was prepared in a black 96-well plate. For the X-ray-excited persistent luminescence, the ZGC nanocubes were illuminated using a veterinary X-ray source with different times (1 Gy min$^{-1}$, 160 kV, 20 mA). Following X-ray exposure, the samples were allowed to rest for 1 min prior to IVIS imaging to monitor persistent luminescence. The IVIS exposure time was fixed at 30 s with a filter to collect the emission at 700 nm.

Cell Viabilities of X-Ray Irradiation with Cell Counting Kit—8 Assay (CCK—8)

Hepatocellular carcinoma cell line (HepG2-Red-FLuc cells) were cultured in a 96-well plate with 5000 cells per well. The plate was pre-incubated for 24 h at 37° C., 5% CO$_2$ in a humidified incubator. X-ray irradiation was performed using a 6 MV Varian-21EX linear accelerator with an irradiation field of 15×15 cm. The irradiation doses varied from 0 to 3 Gy. 10 μl of CCK-8 solution was then added to each well, and the plate was incubated for 4 h before measuring the absorbance at 450 nm using a microplate reader (MULTISKAN FC, Thermo Scientific).

Cell Imaging of PEGylated ZGC Nanocubes and Aggregated ZGC Nanoparticles

HepG2-Red-FLuc cells were cultured in a chambered borosilicate coverglass with 20,000 cells per well and incubated for 24 h at 37° C., 5% CO$_2$ in a humidified incubator. After treatment with either 20 ppm ZGC or aggregated NPs for 6 h, the remaining nanoparticles were washed out by PBS and fresh culture medium was added. Irradiation was performed using a 6 MV Varian-21EX linear accelerator with an irradiation field of 10×10 cm with a dose of 0.5 Gy. Live cell images were captured by a fluorescence microscope (Cell R, Olympus).

Safety Impact of X-Ray Irradiation to Animal

C57BL/6 mice (male, 8-12 weeks old) were purchased from the Laboratory Animal Center of the National Science Council. The healthy mice were subjected to total body irradiation with doses ranging from 0 to 5 Gy using a 6 MV Varian-21EX linear accelerator. After 2 weeks, the mice were sacrificed to collect multiple organs, peripheral blood samples and bone marrow cells for further analysis. Cell damage to the multiple organs was determined by immunohistochemistry. Peripheral blood cell counts of leukocytes, erythrocytes, and platelets were analyzed using a hematology analyzer. Bone marrow cells from femurs and tibias were analyzed for hematopoietic stem cells population by flow cytometry.

Flow Cytometry Analysis

Bone marrow cells from femurs and tibias subjected to X-ray irradiated mice were harvested to determine the population of hematopoietic stem cells c-Kit$^+$Sca-1$^+$Lin$^-$ (KSL) and SLAM$^+$ KSL cells. The cells were stained with PE Sca-1, PerCP-Cy5.5 lineage antibody (BD Biosciences), PE-Cy7 CD117 (c-Kit), FITC CD48 and APC CD150 (BioLegend) for 30 min. The stained cells were analyzed on the LSR II flow cytometer (BD Biosciences) and data analysis was performed using FlowJo software.

X-Ray Excited Radioluminescence of PEGylated ZGC Nanocubes and Aggregated ZGC Nanoparticles in Healthy Mice BALB/c and NOD/SCID nude mice were injected via tail vein with 2 mg/mice of the PEGylated ZGC nanocubes or aggregated ZGC NPs, and the control group was administered with PBS. The mice were subjected to total body irradiation with 0.5 Gy using a 6 MV Varian-21EX linear accelerator. Live mice images were captured by IVIS Spectrum (PerkinElmer) in bioluminescence mode at different time points. The mice were sacrificed at 5 h post-injection to capture ex vivo images of the isolated organs. Data analysis was performed using Living Image software.

The Hepatocellular Carcinoma Animal Model for In Vivo Imaging

In vivo studies were performed in NOD/SCID nude mice (male, 8-12 weeks old). 2×10$^6$HepG2-Red-Fluc cells resuspended in 100 µL phosphate-buffered saline (PBS) were surgically implanted into either the right lobe of the liver through a right flank incision or the left lobe with a midline abdominal incision. The mice underwent bioluminescence imaging 14 days after implantation and bioluminescence flux was recorded to assess tumor growth with D-Luciferin injection (Caliper Life Sciences), and were subjected to in vivo imaging (IVIS, PerkinElmer, Waltham, Mass.) in bioluminescence mode (emission wavelength of 560 nm). A pseudo color image representing the spatial distribution of photon counts was projected onto the photographic image.

X-Ray Excited Radioluminescence of PEGylated ZGC Nanocubes in Hepatocellular Carcinoma Animal Mode.

The tumor-bearing nude mice were injected via tail vein with 2 mg/mice of the PEGylated ZGC nanocubes, while the control group was administered with PBS. The mice were subjected to full body irradiation with 0.5 Gy using a 6 MV Varian-21EX linear accelerator. Live mice images were captured by IVIS Spectrum (PerkinElmer) in bioluminescence mode at different time points. The mice were sacrificed at 4 h post-injection to capture ex vivo images of the isolated organs and tumor tissue. Data analysis was performed using Living Image software.

Statistical Analysis. Group comparisons were performed using the two-tailed Student's t-test. $p<0.05$ was considered to be significant.

Example 1

Characterization of the Present ZGC Nanocubes 1.1 ZGC Concave Nanocubes

The ZGC concave nanocubes were prepared in accordance with procedures described in the "Materials and Methods" section. The thus produced ZGC nanocubes were subjected to image and X-ray analysis, and results are illustrated in FIG. 1.

The transmission electron microscopy (TEM) photo in FIG. 1A showed that ZGC nanocubes dispersed in toluene exhibited uniform morphology. Further, the TEM image of a single nanocube at higher resolution suggested that the nanocube has a concave surface (FIG. 1B). Accordingly, the nanocube was tilted for 5 to 30 degrees from the electron beam to give a better visualization of the morphology (FIG. 1C). The dark part indicated deep dents in the structure, a clear indication of a concave rather than flat surface. The electron diffraction pattern identified the concave nanocube as a single crystalline of cubic spinel structure (FIG. 1D). Image taken from the center of the nanocube showed fringe spacing of 0.29 nm corresponding to the {220} basal plane (FIG. 1E). Further, an HRTEM image indicated the edge of the concave nanocube as a stepped facet consisting of {220} and {400} facets (FIG. 1F). XRD patterns confirmed a cubic spinel structure of ZGC (FIG. 1G).

When the ZGC concave nanocubes were excited by UV light at 250 nm, a broad emission band appeared in the NIR rang with a peak at 695 nm with a shoulder around 715 nm (FIG. 1H), the finding was consistent with previous reports that these two peaks belong to the zero phonon line at 695 nm attributed to Cr$^{3+}$ ions with a neighboring antisite defect, referred to as Cr$_{N2}$, and the Stokes phonon side band (at 715 nm, Cr$^{3+}$ in a normal spinel environment results in R lines consisting of stokes and anti-stokes phonon side bands, referred to as Cr$_R$. We found the emission intensity of ZGC revealed a Cr-concentration-dependent behavior. The strongest emission can be seen in 1% Cr dopant that was chosen for the later in vitro and in vivo studies.

1.2 PEGyated and APTES-Modified ZGC Nanocubes

To render the ZGC nanocubes of Example 1.1 suitable for biological application, they were further modified with (3-aminopropyl)triethoxysilane (APTES) and PEG molecules in accordance with procedures described in the "Materials and Methods" section.

1.2.1 APTES Modified ZGC Nanocubes

To render the ZGC nanocubes of Example 1.1 hydrophilic, they were modified with APTES. The photos in FIG. 1I clearly showed that the nanocubes features changed before and after APTES modification. Significant aggregation was seen in H$_2$O before modification, which changed to a dispersed status after modification. Fourier-transform infrared (FTIR) measurements also confirmed the presence of APTES on the nanocube surface, in which peaks at 1081, 774 and 485 cm$^{-1}$ were associated with Si—O—Si stretching, 1600 and 1640 cm$^{-1}$ were associated with NH$_2$ bending and 3363 and 3282 cm$^{-1}$ were associated with NH$_2$ stretching. The stretching peak at 1296 cm$^{-1}$ was associated with C—N. (data not shown).

1.2.2. Pegylated and APTES Modified ZGC Nanocubes

In this example, the APTES modified nanocubes of Example 1.2.1 were further modified with PEG molecules. Signal at 1034 cm$^{-1}$ corresponding to the C—O stretching mode was observed for PEGylated ZGC from FTIR spectrum. Since the surface group of ZGC modified by APTES and PEG was amine group, similar bands corresponding to NH$_2$ was observed (data not shown). The zeta potential and hydrodynamic diameter were also determined after each step of modification to confirm the successful functionalization onto the ZGC nanocubes. The TGA analysis revealed a weight loss of about 10% and 11.4% for APTES-modified and PEGylated ZGC, respectively. From the loss of weight, the quantification of PEG was determined to be 1.4% (data not shown).

1.3 Persistent Luminescence of ZGC of Example 1.2.2 Upon Irradiation

Figure 2:
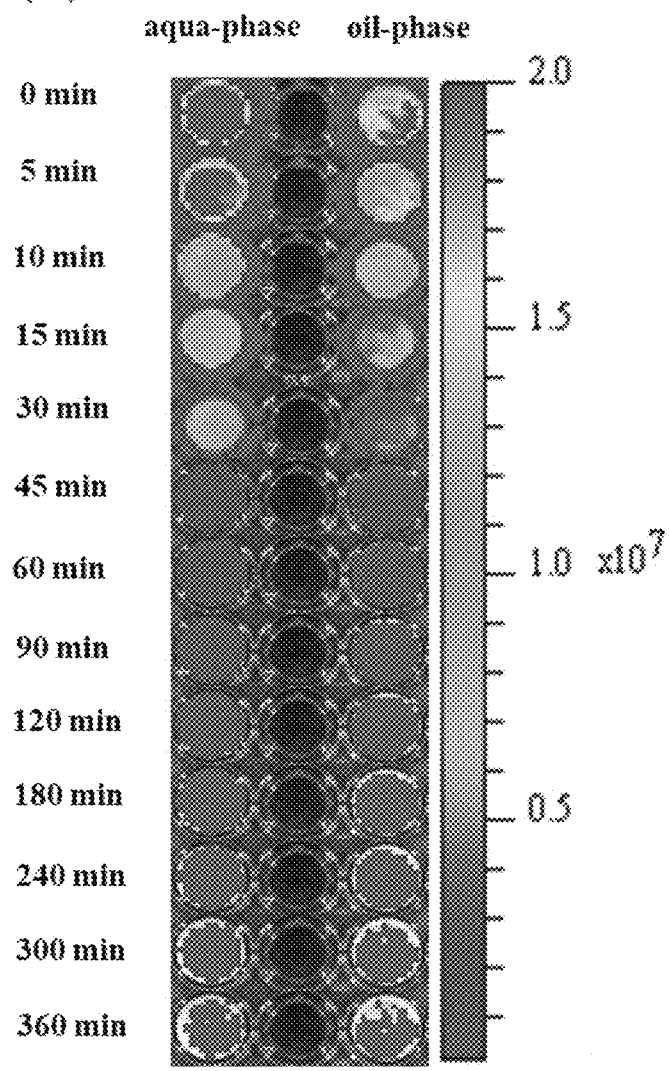
FIG. 2 Comparison of the long-lasting luminescence property of oil-phase and aqueous-phase ZGC nanocubes excited by a mercury lamp. (A) Long-lasting luminescence decay curves after 1 min mercury lamp exposure (inset shows the zoomed-in decay curves) and (B) corresponding long-lasting luminescence images subjected to IVIS capture set at 30 s of the exposure time after excitation ceased. (C, D) Each re-charging decay curve recorded 1 min following excitation and (E) corresponding long-lasting luminescence images. Statistical analysis was performed using the two-tailed Student's t-test (**p<0.01)
Figure 2:
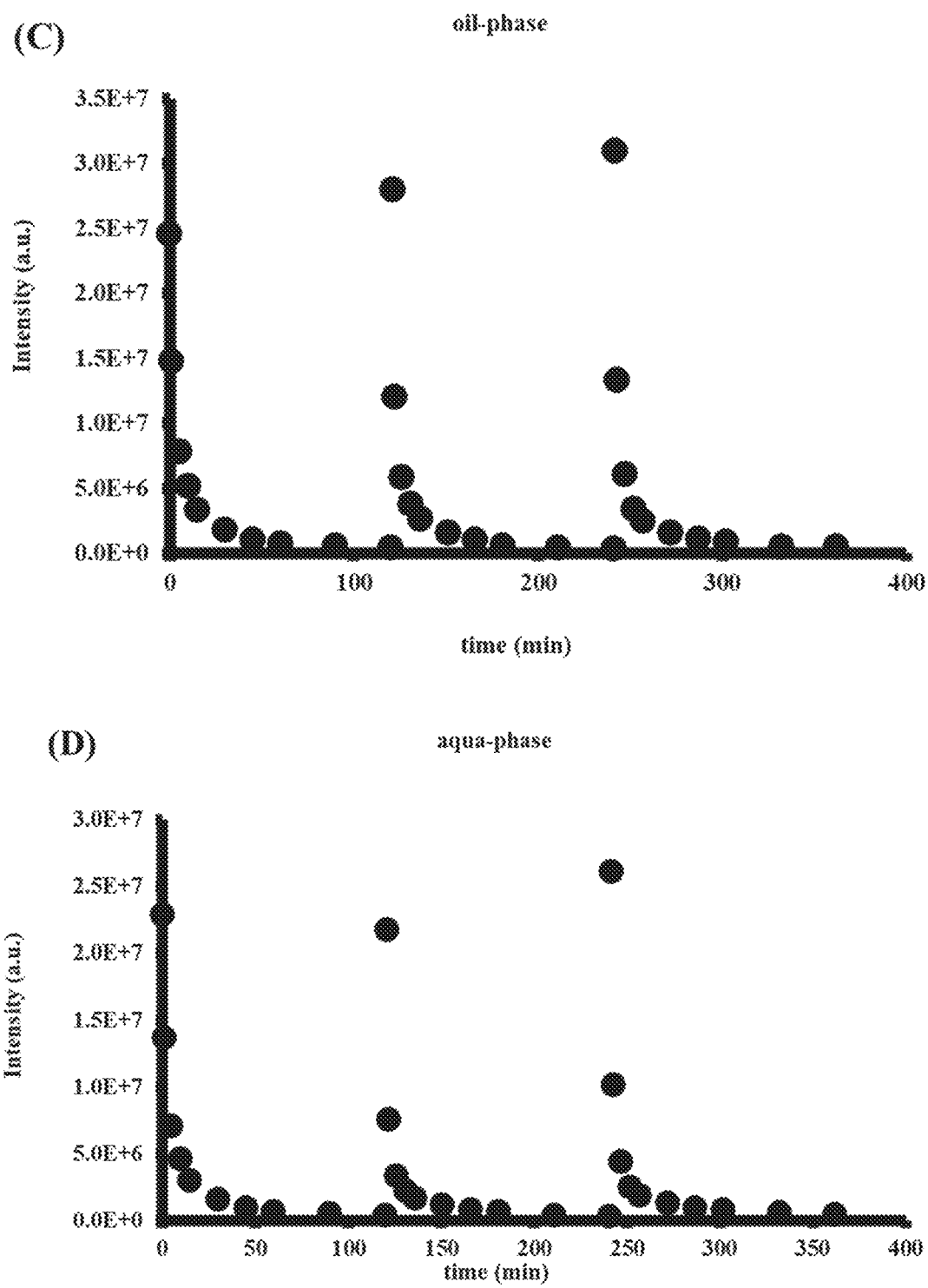
Figure 2:
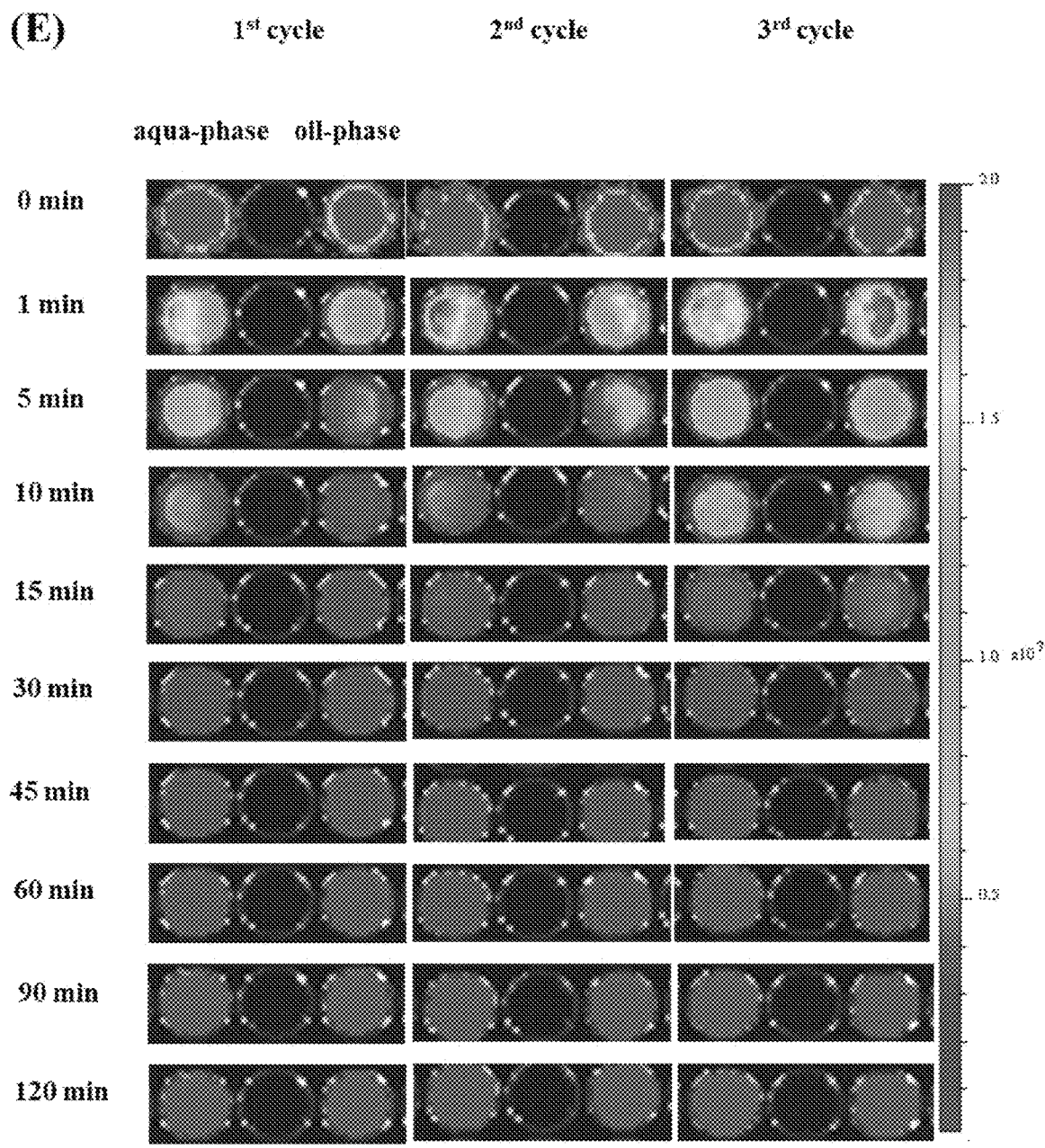

ZGC nanocubes of Example 1.2.2 excited at 250 nm emitted NIR at 695 nm. The LLL was studied after 1 min of mercury lamp exposure, and then subjected to In Vivo Image System (IVIS) analysis, in which images were captured at 30 s of exposure time with a 700 nm filter. The LLL intensity and decay behavior of the oil-phase and aqueous-phase ZGC nanocubes were quantified by region of interest (ROI) analysis. Both oil-phase and aqueous-phase ZGC nanocubes exhibited similar LLL decay curves with a lifetime of 6 hr, a 10-fold increase in LLL intensity over background (FIGS. 2, (A) and (B)). The LLL decay curves of the oil-phase and aqueous-phase ZGC nanocubes could be recharged and remained unaffected during 3 repeated excitations (FIGS. 2, (C), (D), and (E)). The resulting ZGC concave nanocubes were stable through repeated excitation and maintained their LLL behavior.

Figure 3:
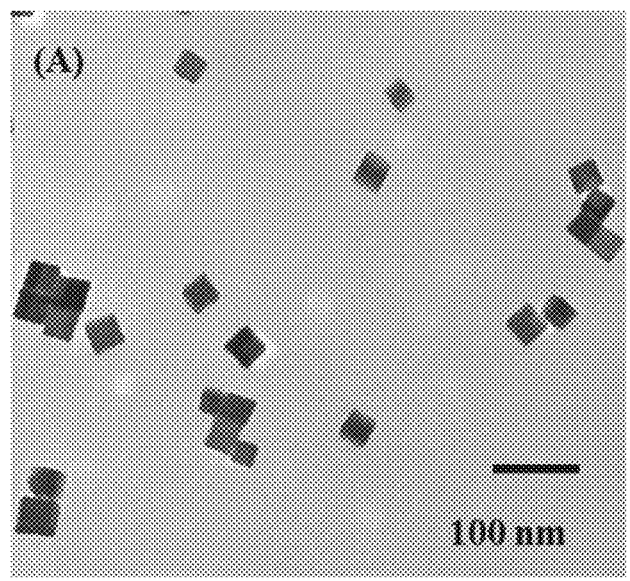
FIG. 3 Comparison of the long-lasting luminescence property of PEGylated ZGC nanocubes and aggregated nanoparticles excited by mercury lamp. (A) TEM image of the APTES modified ZGC nanocubes. (B) TEM image of the aggregated ZGC nanoparticles synthesized in aqueous solution. (C) Long-lasting luminescence decay curves after 1 min mercury lamp exposure (inset shows the zoomed-in decay curves of the aggregated nanoparticles). (D) Corresponding long-lasting luminescence images subjected to IVIS capture set at 30 s of the exposure time after excitation ceased. Statistical analysis was performed using the two-tailed Student's t-test (**p<0.01)
Figure 3:
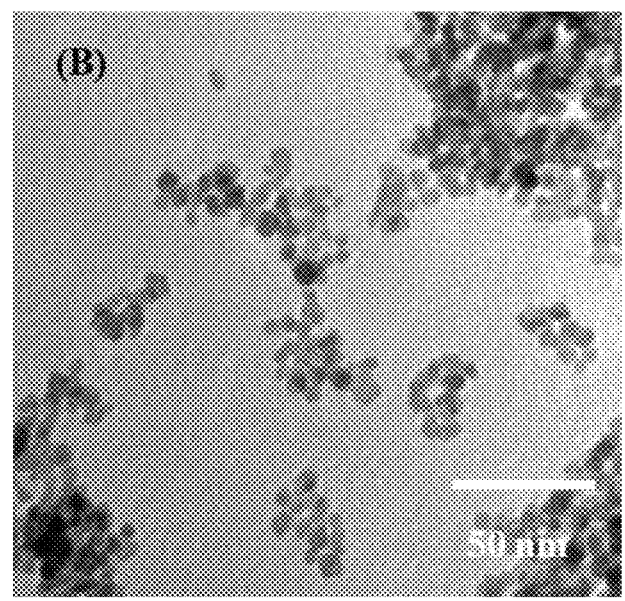
Figure 3:
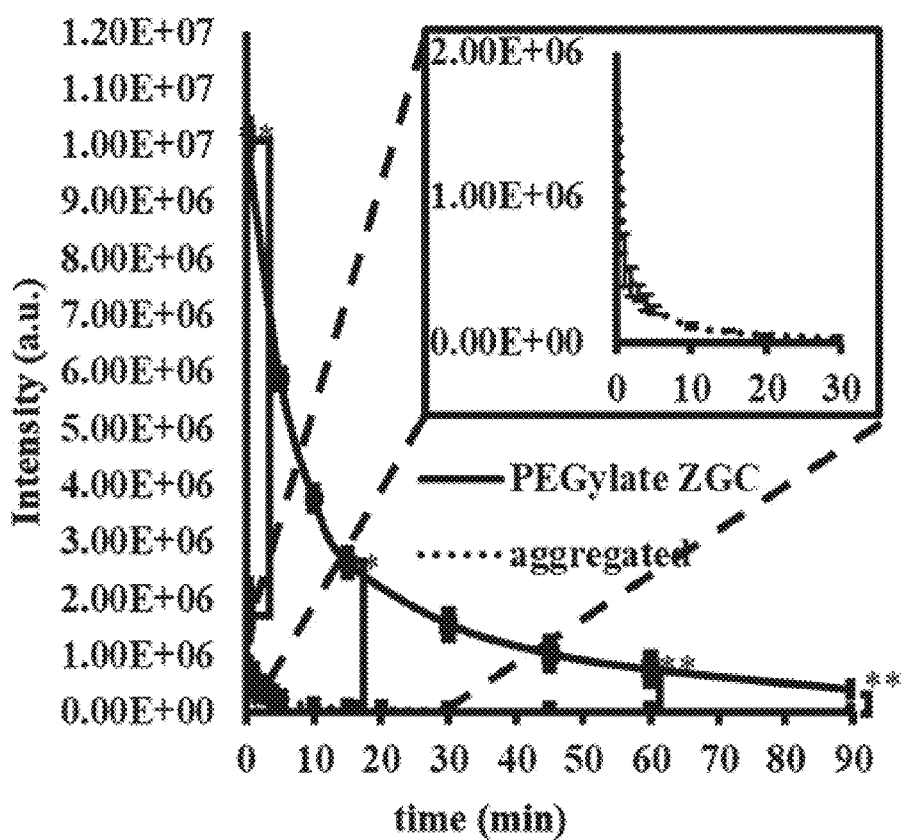
Figure 3:
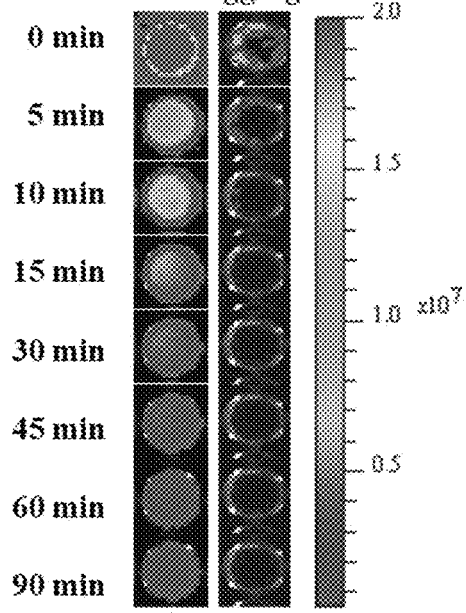

For comparison, aqueous-phase ZGC nanoparticles were prepared by a previously described method (Wang J et al., 2015, J. Am. Chem. Soc. 137: 5304). The as-prepared aqueous ZGC nanoparticles (FIG. 3, (B)) were more likely to aggregate than the present APTES modified ZGC nanocubes of Example 1.2 (FIG. 3, (A)), and exhibited as a mixture of cubic and sphere-like shapes about 6 nm in size. Further, the compared ZGC remained a cubic spinel with a highly crystalline structure, and emitted LLL as well, but the luminescent intensity was 5-fold less than that of the PEGylated ZGC concave nanocubes of Example 1.2 based on the intensity captured at 30 s of the exposure time after excitation ceased (FIGS. 3, (C) and (D)). In addition, the LLL of the as-prepared aqueous ZGC nanoparticles lasted for 30 min to reach the background signal level (inset of FIG. 3, (C)) while the PEGylated ZGC concave nanocubes can prolong emission up to 6 h (inset of FIG. 2, (A)).

1.4 Persistent Luminescence of the ZGC of Example 1.2.2 Upon X-Ray Irradiation

Figure 4:
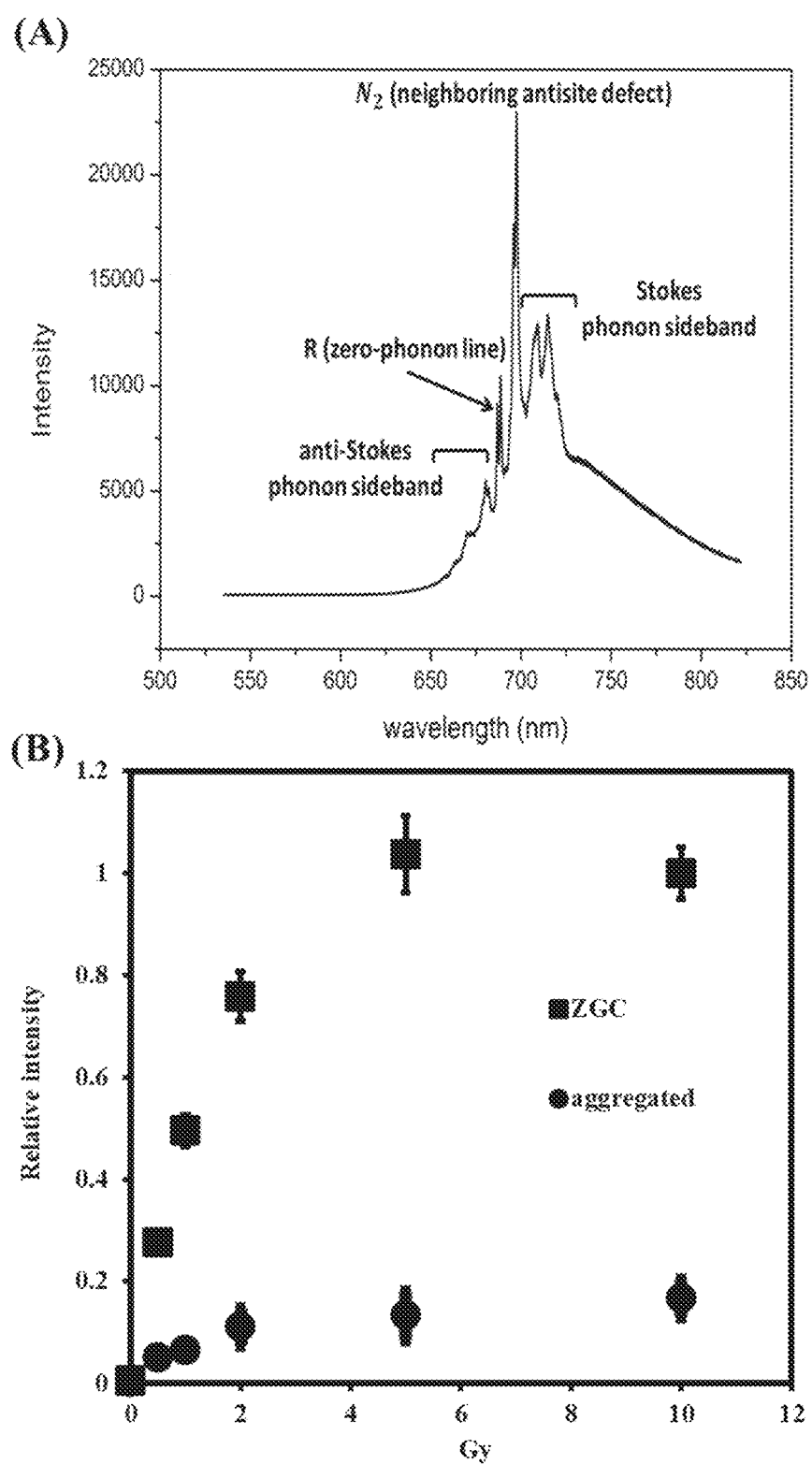
FIG. 4 Luminescent behavior upon X-ray excitation. (A) X-ray excited radioluminescence of concave nanocubes under synchrotron radiation source. (B) X-ray excited radioluminescent intensity as a function of X-ray dose for ZGC nanocubes and aggregated nanoparticles following excitation using a veterinary X-ray source (1 Gy $min^{-1}$, 160 kV, 20 mA). (C) Comparison of the long-lasting luminescence property of PEGylated ZGC nanocubes and aggregated nanoparticles following 0.5 and 1 Gy of X-ray excitation. (D) Corresponding long-lasting luminescence images of PEGylated ZGC nanocubes and aggregated nanoparticles subjected to IVIS capture after X-ray excitation ceased. Statistical analysis was performed using the two-tailed Student's t-test (**p<0.01)
Figure 4:
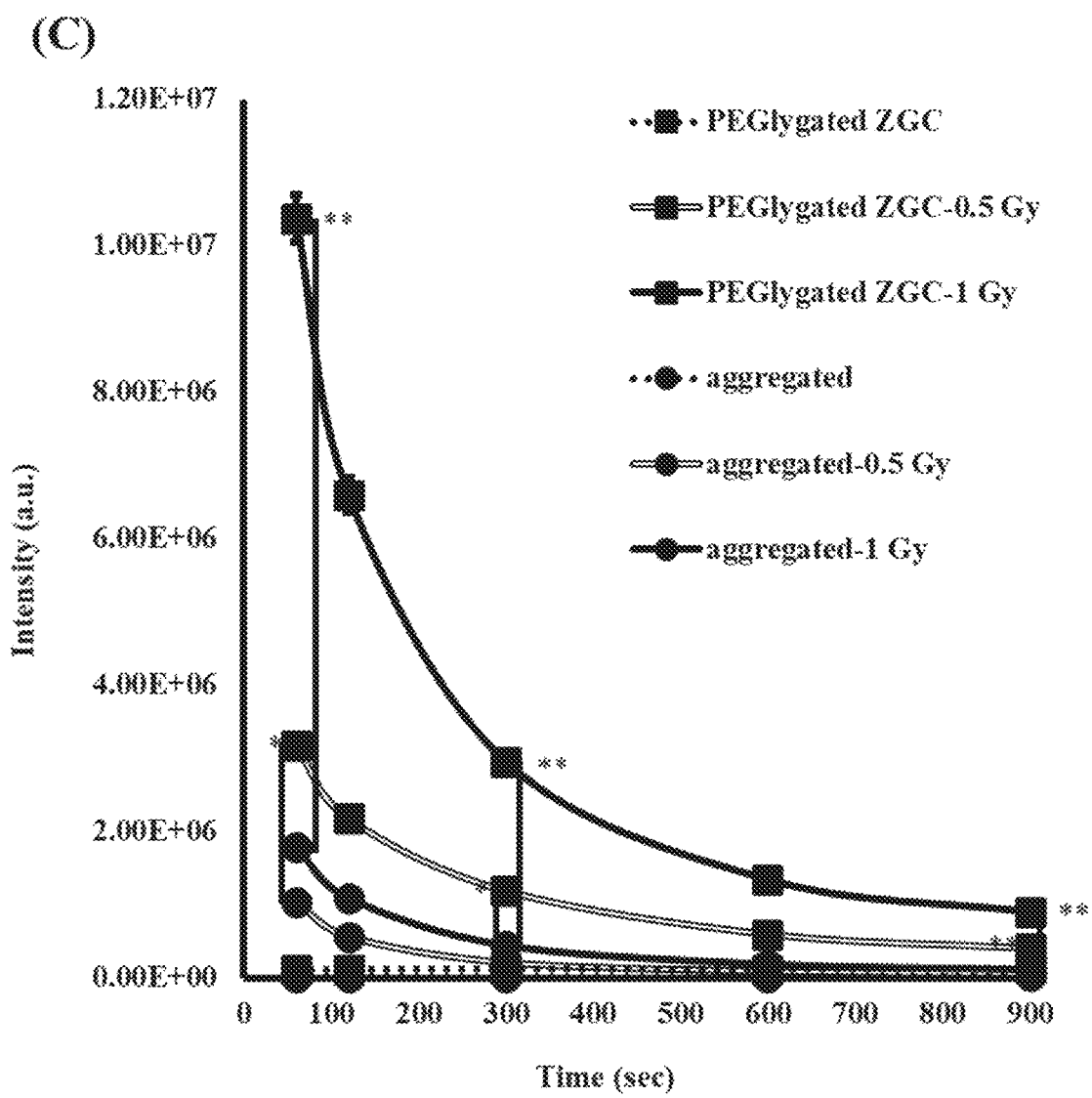
Figure 4:
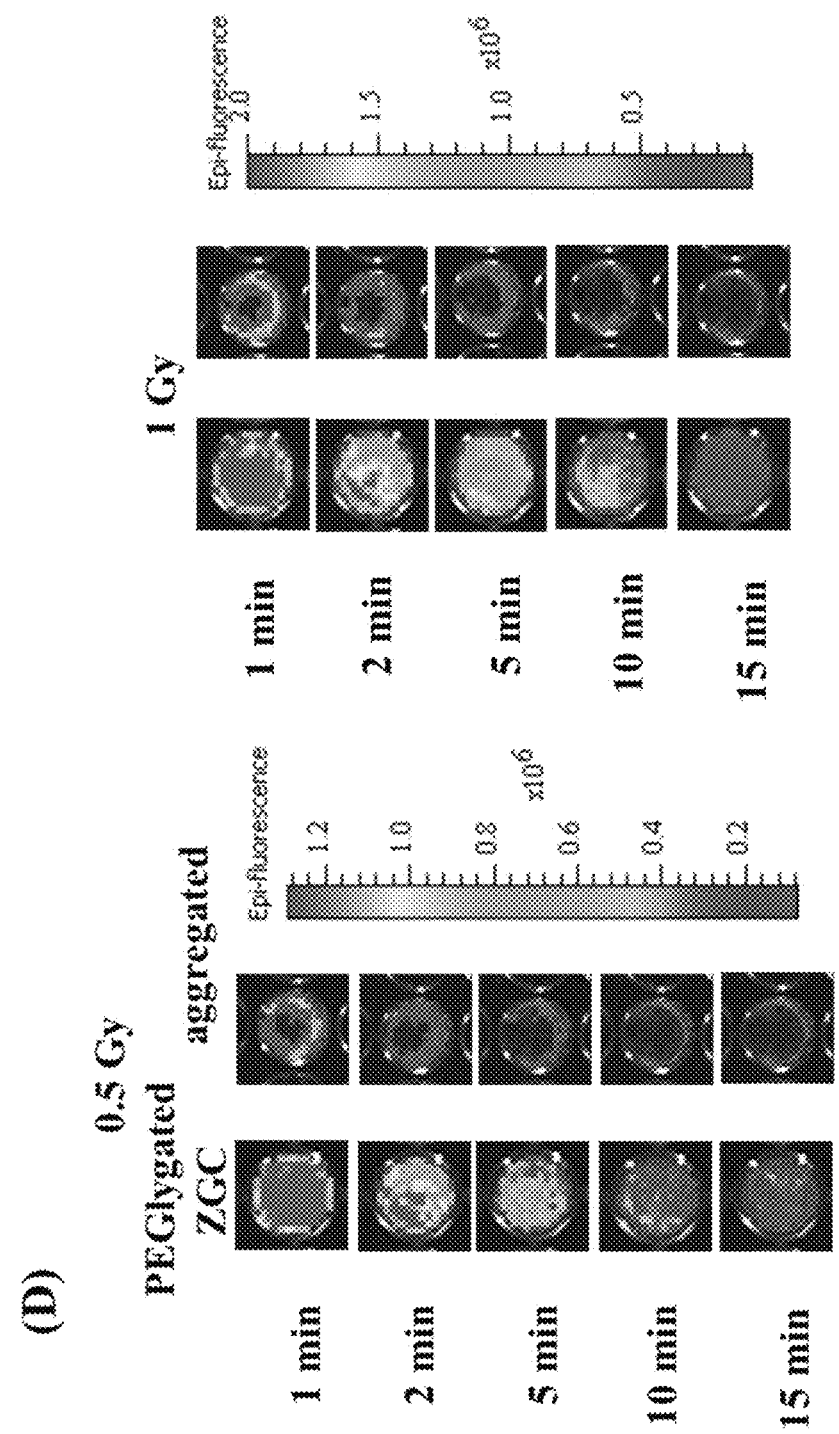

The X-ray excited radioluminescence (XRL) of the nanocubes of Example 1.2.2 is illustrated in FIG. 4, (A). The same emission band was obtained as that for UV excitation (FIG. 1, (H)), but with well-resolved peaks consisting of $Cr_{N2}$ and $Cr_R$ lines as well as Stokes and anti-Stokes phonon sidebands. The emission peaks appearing at 686.78 nm and 688.69 nm were respectively two zero phonon lines known as R2 and R1 for the $^2E \rightarrow {}^4A_2$ transition of $Cr^{3+}$. The phonon side bands (PSB) of the R lines were identified at 708.9 nm, 714.82 nm and 720.15 nm for the Stokes PSB and at 669.95 nm and 680.24 nm for the anti-Stokes PSB. The structure-dependent lines at ~696.7 nm were assigned to N2. Next, a veterinary X-ray source (1 Gy $min^{-1}$, 160 kV, 20 mA) was used to excite the ZGC nanocubes and agglomerative nanoparticles for XRL. Both particles displayed increasing luminescent intensity as a function of X-ray dose before 5 Gy, but reached a plateau after 5 Gy (FIG. 4, (B)). ZGC nanocubes revealed a much stronger emission intensity than that of agglomerative nanoparticles. In fact, using a low dose of 0.5 Gy still offered an appreciable radioluminescence for ZGC nanocubes 5-times that of the agglomerative nanoparticles. The LLL decay taken after excitation ceased at 0.5 and 1 Gy for both nanoparticles (FIGS. 4, (C) and (D)). Clearly, PEGylated ZGC nanocubes exhibited a much greater emission intensity and longer-lasting luminescence compared to the agglomerative nanoparticles. For example, LLL reached background after 10 min when excitation at 0.5 Gy ceased for agglomerative nanoparticles, while the luminescence for the PEGylated ZGC nanocubes continued for 15 min.

Example 2

In Vitro and In Vivo Persistent Luminescence of ZGC Nanocubes of Example 1.2.2 Upon X-Ray Irradiation In this example, the ZGC nanocubes of Example 1.2.2 were subjected to in vitro and in vivo luminescence analysis.

Figure 5:
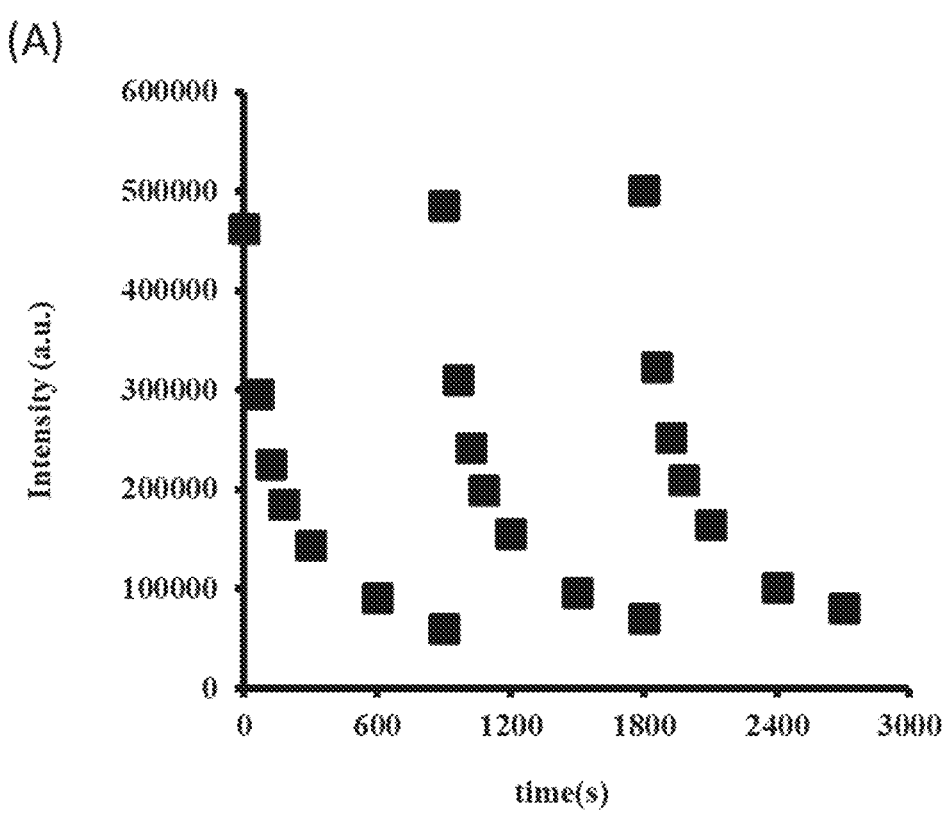
FIG. 5 Long-lasting luminescence for hepatocellular carcinoma cells (HepG2-Red-FLuc) with PEGylated ZGC nanocubes following excitation using a clinical X-ray linear accelerator. (A) Re-charging decay curves of PEGylated ZGC nanocubes recorded following 0.5 Gy of X-ray irradiation. (B) Corresponding re-charging decay images subjected to IVIS capture.
Figure 5:
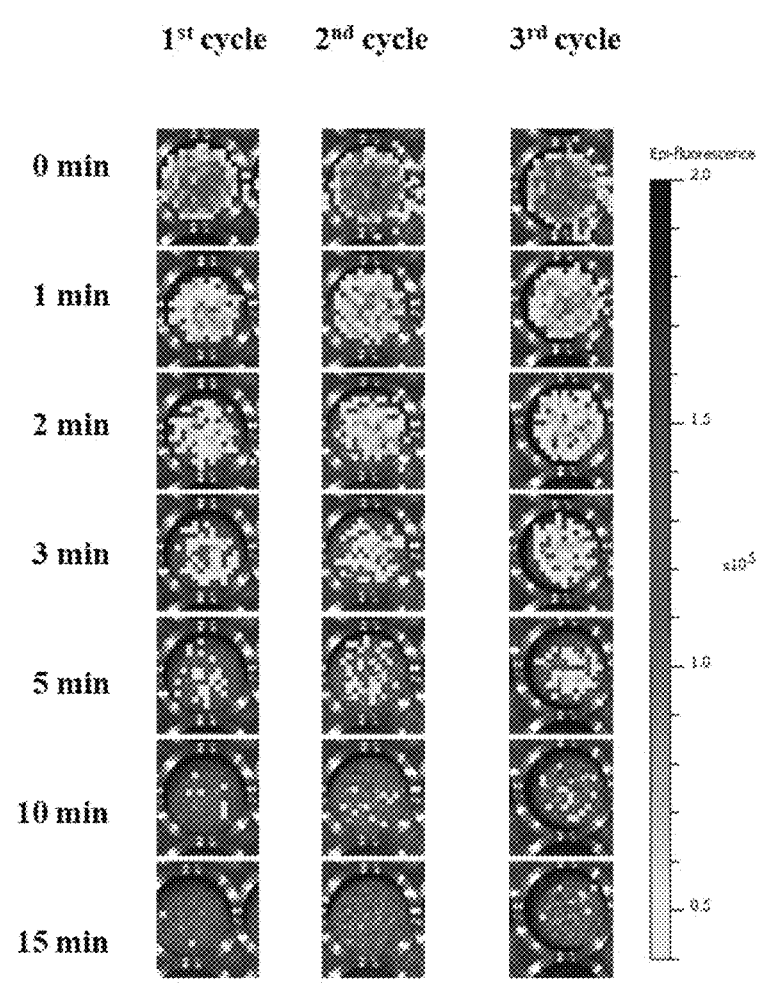

For in vitro study, it was found that no apparent change in cell viability with (0.5 Gy)/without X-ray exposure for the cells incubated with PEGylate ZGC. The structural stability of the PEGylated ZGC was examined and was then dispersed in $H_2O$ and phosphate-buffered saline (PBS) at pH 7, PBS at pH 5, fetal bovine serum (FBS), and medium (DMEM) for 5 days of observation. It was found that the good stability of PEGylated ZGC nanocubes after 5 days under different storage conditions. Cells incubated with PEGylated nanocubes can be readily seen for LLL and can be repeatedly stimulated with consistent emission intensity and decay behavior (FIGS. 5, (A) and (B)), while no observable signal was detected for cells incubated with agglomerative ZGC (data not shown).

Figure 6:
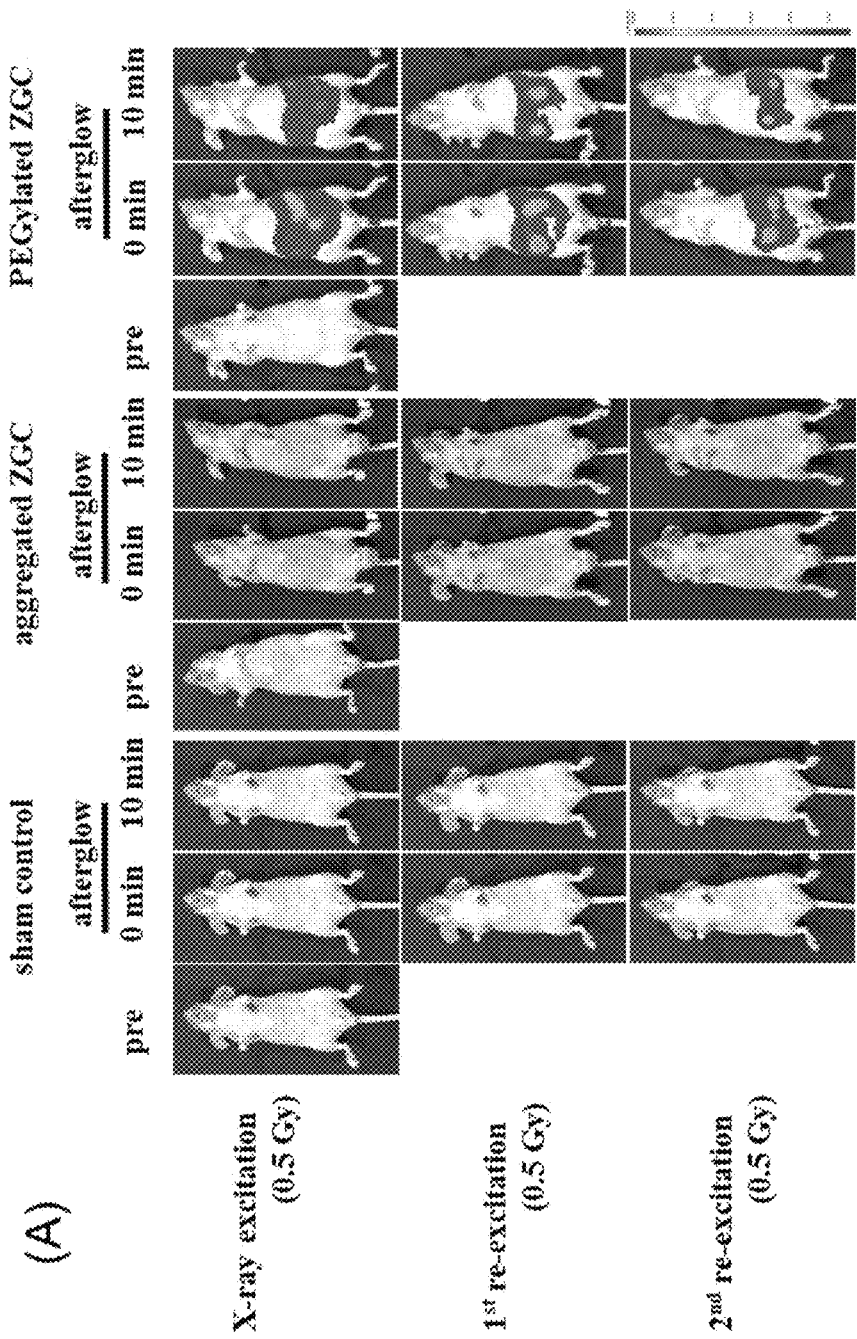
FIG. 6 In vivo and ex vivo bioluminescence of the respective intravenous injection of PBS, aggregated ZGC nanoparticles, and PEGylated ZGC nanocubes for the healthy mice following excitation using a clinical X-ray linear accelerator. (A) In vivo long-lasting luminescence imaging acquired immediately (0 min) and 10 min following 0.5 Gy of X-ray irradiation. (B) Ex vivo imaging from the dissected tissues corresponding to (A) captured for the long-lasting luminescence 5 h after 0.5 Gy of X-ray irradiation ceased and re-charging images.
Figure 6:
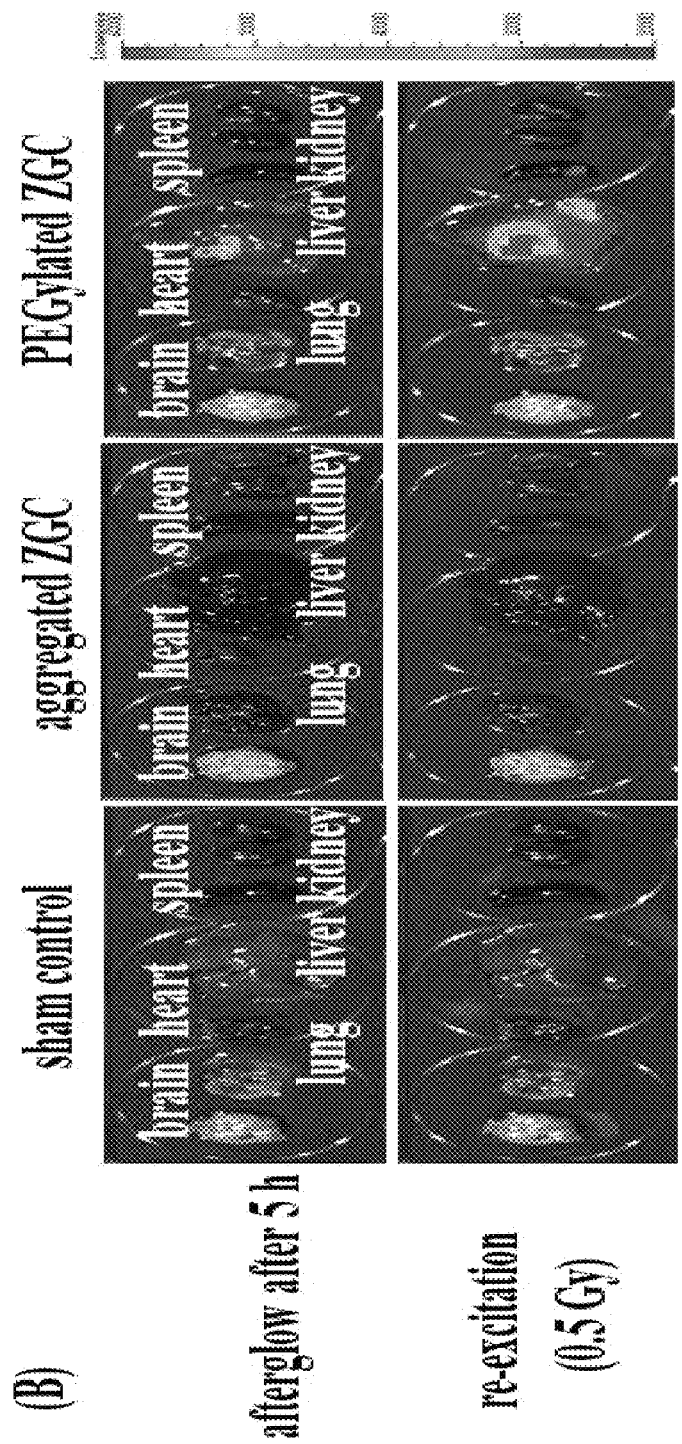

For in vivo studies, PEGylated ZGC of Example 1.2.2 and aqueous-phase ZGC nanoparticles were respectively administrated through the tail vein of nude mice (n=3), followed by a dose of 0.5 Gy using clinical X-ray excitation. Consistent with in vitro observations, only the groups treated with PEGylated ZGC of Example 1.2.2 exhibited a bright afterglow in the liver region without significantly compromising imaging quality over the repeated stimulations (FIG. 6, (A)). For example, the signal intensity was $1.04 \times 10^6$ p $s^{-1}cm^{-2}sr^{-1}$ immediately following X-ray excitation. Following the re-excitation process, the signal intensities decreased slightly with $0.78 \times 10^6$ p $s^{-1}cm^{-2}sr^{-1}$ for $1^{st}$ re-excitation and $0.77 \times 10^6$ p $s^{-1}cm^{-2}sr^{-1}$ for $2^{nd}$ re-excitation immediately after X-ray excitation ceased. Contrarily, no LLL signals can be seen in the sham control and the aggregated ZGC nanoparticle groups following X-ray excitation. The ex vivo clearly demonstrated PEGylated ZGC predominantly accumulated in the liver, showing continuous emissions 5 h following X-ray excitation (FIG. 6, (B)). Re-charging brightened liver tissue was seen. Signal in the spleen indicated a certain accumulation of PEGylated ZGC nanocubes of Example 1.2.2. Additionally, we also examined the healthy mice for the LLL efficiency of PEGylated ZGC nanocubes with one-time X-ray excitation. The signal intensity was $4.18 \times 10^5$ p $s^{-1}cm^{-2}sr^{-1}$ immediately following X-ray excitation and then decreased to $1.01 \times 10^5$ p $s^{-1}cm^{-2}sr^{-1}$ after post 60 min (data not shown). After post 90 min, the LLL signal cannot be detected with optical imaging.

Figure 7:
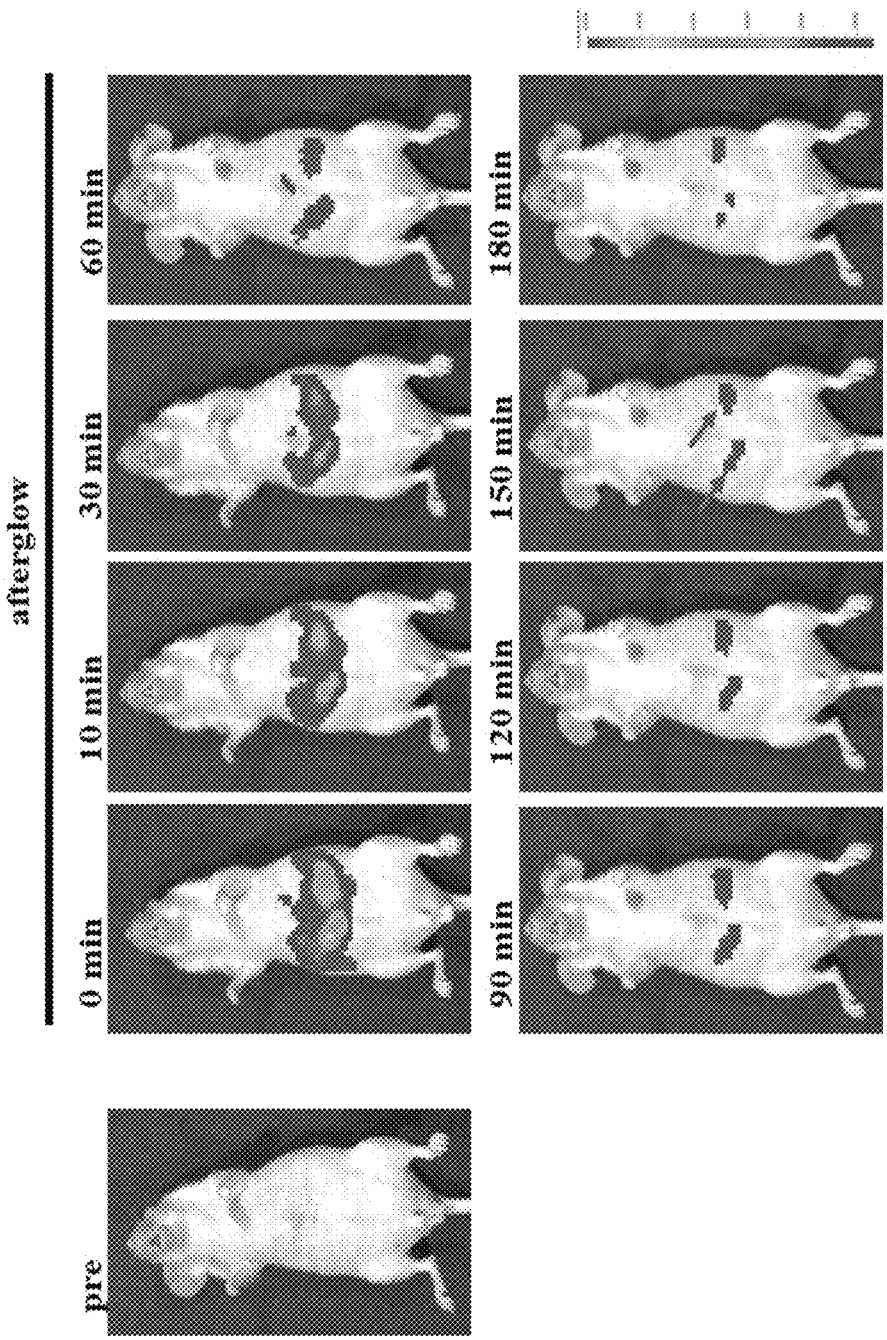
FIG. 7 In vivo and ex vivo bioluminescence of the intravenous injection of PEGylated ZGC nanocubes for tumor-bearing mice following excitation using a clinical X-ray linear accelerator. (A) In vivo long-lasting luminescence imaging acquired immediately (0 min) to 180 min following 0.5 Gy of X-ray irradiation (red arrow: tumor region; blue arrow: spleen). (B) Ex vivo imaging from the dissected tissues corresponding to (A) captured for the long-lasting luminescence 4 h after 0.5 Gy of X-ray irradiation ceased and re-charging images.

Because the majority of accumulation was observed in the liver, we further investigated specific passive targeting of an orthotopic hepatic tumor established with HepG2 cells. First, bioluminescence was used to evaluate tumor growth in the liver. The tumor-bearing mice injected with D-luciferin confirmed the presence of tumors in the liver (data not shown). Tumor-bearing mice were then intravenously injected with PEGylated ZGC nanocubes of Example 1.2.2, whom exhibited an afterglow with continuous emission for 3 h in the hepatic tumor (FIG. 7, (A)) after 0.5 Gy X-ray excitation. The signal intensity was $1.65 \times 10^4$ p $s^{-1}cm^{-2}sr^{-1}$ immediately following excitation and gradually decreased to $4.93 \times 10^3$ p $s^{-1}cm^{-2}sr^{-1}$ after 3 h. The mice were sacrificed at 4 h post-injection to capture ex vivo images of the isolated organs (FIG. 7, (B)). Ex vivo in the afterglow and re-charging images confirmed highly specific tumor uptake. Whereas the healthy mice exhibited brightening in nearly the whole liver (FIG. 6, (B)), LLL signals concentrated on the location of tumor area in liver. This indicted that the PEGylated ZGC nanocubes had been uptaken by HepG2 malignant tumors through the enhanced permeability and retention (EPR) effect and retained in the tumor region.

Taken together, in vivo and ex vivo studies of tumor-bearing animal models confirmed the PEGylated ZGC nanocubes of Example 1.2.2 may serve as a luminescent probe in hepatic tumor imaging.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A modified chromium-doped zinc gallate (ZGC) nanocube characterized in having a concave surface, wherein the concave surface is modified with (3-aminopropyl)triethoxysilane (APTES) thereby rendering it hydrophilic.

2. The modified ZGC nanocube of claim 1, further comprising a plurality of polyethylene glycol (PEG) molecules independently linked to the APTES via an amide bond formed there between.

3. The modified ZGC nanocube of claim 2, wherein the modified ZGC nanocube produces long lasting luminescence (LLL) that lasts for at least 1.5 hours after being excited with a dose of X-ray.

4. The modified ZGC nanocube of claim 3, wherein the modified ZGC nanocube produces LLL that lasts for at least 3 hours.

5. The modified ZGC nanocube of claim 4, wherein the modified ZGC nanocube produces LLL that lasts for at least 5 hours.

6. A method of producing a modified ZGC nanocube, comprising:
   (a) respectively reacting zinc nitrate and gallium nitrate with a base, thereby forming zinc hydroxide and gallium hydroxide;
   (b) mixing the zinc hydroxide and the gallium hydroxide respectively produced in the step (a) and chromium nitrate with water to give a first mixture;
   (c) adding a chelating agent and toluene to the first mixture to give a second mixture;
   (d) autoclaving the second mixture to produce a ZGC nanocube; and
   (e) silanizing the ZGC nanocube with (3-aminopropyl) triethoxysilane (APTES) to produce the modified ZGC nanotube.

7. The method of claim 6, wherein
   in the step (a), the base is ammonium hydroxide, sodium hydroxide or potassium hydroxide; and
   in the step (c), the chelating agent is $C_{16-20}$ fatty acid, carboxylated PEG or ascorbic acid.

8. The method of claim 7, wherein in the step (a), the base is ammonium hydroxide; and in the step (c), the chelating agent is oleic acid.

9. The method of claim 6, wherein,
   in the step (d), the autoclave is conducted at a temperature of 220° C. for 3 days; and
   in the step (e), the silanization is conducted at a temperature of 60° C. for 18 hours.

10. The method of claim 6, further comprising,
    (f) pegylating the modified ZGC nanocube by reacting with amine-PEG-acid in the presence of 1-Ethyl-3-(3-dimethylaminopropyl)carbodiimide (EDC) and N-hydroxysuccinimide (NHS), thereby producing a pegylated modified ZGC nanocube, in which the amine-PEG-acid has a molecular weight of about 3,400.

11. The method of claim 10, wherein the modified ZGC nanocube and the pegylated modified ZGC nanocube respectively produce long lasting luminescence (LLL) that lasts for at least 1.5 hours after being excited with X-ray.

12. The method of claim 11, wherein the modified ZGC nanocube and the pegylated modified ZGC nanocube respectively produce LLL that lasts for at least 3 hours after being excited with X-ray.

13. The method of claim 11, wherein the modified ZGC nanocube and the pegylated modified ZGC nanocube respectively produce LLL that lasts for at least 5 hours after being excited with X-ray.

14. A method of imaging an area of interest (AOI) in a subject comprising:
    (a) administering a sufficient amount of the modified ZGC nanocube of claim 2 to the AOI; and
    (b) irradiating the subject with a dose of X ray thereby producing the image of the AOI.

15. The method of claim 14, wherein the dose of X ray is no more than 3 Gy.

16. The method of claim 15, wherein the dose of X ray is about 0.5 Gy.

17. The method of claim 14, wherein the AOI is a cancer.

18. The method of claim 17, wherein the cancer is selected from the group consisting of bone cancer, brain cancer, breast cancer, colon cancer, cervical cancer, Ewing's sarcoma, esophageal cancer, hepatic cancer, head and neck cancer, larynx cancer, melanoma, multiple myeloma, nasopharynx cancer, non-small-cell lung cancer, non-melanoma skin cancer, neuroblastoma, pancreatic cancer, prostate cancer, retinoblastoma, rectal cancer, small-cell lung cancer, testicular cancer, thyroid cancer, and Wilms' tumor.

19. The method of claim 14, wherein the modified ZGC nanocube produces long lasting luminescence (LLL) that lasts for at least 1.5 hours.

20. The method of claim 19, wherein the modified ZGC nanocube produces LLL that lasts for at least 3 hours.

21. The method of claim 20, wherein the modified ZGC nanocube produces LLL that lasts for at least 5 hours.

22. The method of claim 14, wherein the subject is a human.

* * * * *